United States Patent
Jonak et al.

(10) Patent No.: US 7,230,083 B2
(45) Date of Patent: Jun. 12, 2007

(54) ANTI-ALPHABETA3 HUMANIZED MONOCLONAL ANTIBODIES

(75) Inventors: Zdenka L Jonak, Devon, PA (US); Kyung O Johanson, Bryn Mawr, PA (US); Alexander Taylor, Newtown Square, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 637 days.

(21) Appl. No.: 10/223,880

(22) Filed: Aug. 20, 2002

(65) Prior Publication Data

US 2003/0152571 A1    Aug. 14, 2003

Related U.S. Application Data

(63) Continuation of application No. 09/380,910, filed as application No. PCT/US98/04987 on Mar. 12, 1998.

(60) Provisional application No. 60/039,609, filed on Mar. 12, 1997.

(51) Int. Cl.
*C07K 16/00*    (2006.01)

(52) U.S. Cl. .................................. 530/387.1

(58) Field of Classification Search ..................... None
See application file for complete search history.

(56) References Cited

U.S. PATENT DOCUMENTS 6,160,099 A * 12/2000 Jonak et al. ........... 530/388.22

FOREIGN PATENT DOCUMENTS

| WO | WO 89/05155 | 6/1989 |
| WO | WO 93/20229 | 10/1993 |
| WO | WO 95/25543 | 9/1995 |

OTHER PUBLICATIONS

Rudikoff et al (Proc Natl Acad Sci USA 1982 vol. 79 p. 1979.*
Riechmann et al., "Reshaping Human Antibodies for Therapy", *Nature*. vol. 332, pp. 323-327 (1988).

* cited by examiner

*Primary Examiner*—Christopher H. Yaen
(74) *Attorney, Agent, or Firm*—Andrea V. Lockenour; Edward R. Gimmi; Charles M. Kinzig

(57) ABSTRACT

This invention relates to novel humanized and other recombinant or engineered antibodies or monoclonal antibodies to the vitronectin $\alpha_v\beta_3$ receptor and to the genes encoding same. Such antibodies are useful for the therapeutic and/or prophylactic treatment of $\alpha_v\beta_3$-mediated disorders, such as restenosis, in human patients.

10 Claims, 8 Drawing Sheets

| mAb | $k_a (M^{-1}s^{-1})$ | $k_d (s^{-1})$ | calculated $K_D$ (pM) |
|---|---|---|---|
| D12 | $7.7 +/- 1.4 \times 10^5$ | $4.1 +/- 0.7 \times 10^{-4}$ | $530 +/- 130$ |
| LM609 | $1.1 +/- 0.4 \times 10^6$ | $5.1 +/- 1.1 \times 10^{-4}$ | $460 +/- 220$ |

ANTI-ALPHABETA3 HUMANIZED MONOCLONAL ANTIBODIES

This is a continuation of application Ser. No. 09/380,910, filed 10 Sep. 1999 now abandoned, which is a 35 U.S.C. §371 National Stage entry of PCT International Application No. PCT/U598/04987, filed 12 Mar. 1998, which claims the benefit from Provisional Application No. 60/039,609, filed 12, Mar. 1997.

FIELD OF THE INVENTION

This invention relates to novel humanized monoclonal antibodies (mAbs) and to the genes encoding same. More specifically, this invention relates to human monoclonal antibodies specifically reactive with an epitope of the human vitronectin receptor, $\alpha_v\beta_3$. Such antibodies are useful for the therapeutic and/or prophylactic treatment of restenosis, angiogenic associated diseases (e.g., cancer, cancer metastasis, rheumatoid arthritis, atherosclerosis) among other disorders.

BACKGROUND OF THE INVENTION

Integrins are a superfamily of cell adhesion receptors, which are heterodimeric transmembrane glycoproteins expressed on a variety of cells. These cell surface adhesion receptors include the vitronectin receptor $\alpha_v\beta_3$. The vitronectin receptor $\alpha_v\beta_3$ is expressed on a number of cells, including endothelial, smooth muscle, osteoclast, and tumor cells, and, thus, it has a variety of functions.

For example, the $\alpha_v\beta_3$ receptor expressed on the membrane of osteoclast cells has been postulated to mediate the bone resorption process and contribute to the development of osteoporosis [Ross, et al., *J. Biol. Chem.*, 1987, 262: 7703]. As another example, the $\alpha_v\beta_3$ receptor expressed on human aortic smooth muscle cells has been postulated to stimulate their migration into neointima, which leads to the formation of atherosclerosis and restenosis after angioplasty [Brown, et al., *Cardiovascular Res.*, 1994, 28: 1815].

The connection between antagonism of the vitronectin receptor and restenosis after vascular procedures was referred to by Choi et al, *J. Vasc. Surg.*, 1994, 19:125–34. International Patent Publication No. WO95/25543, published Mar. 9, 1995, refers to a method of inhibiting angiogenesis by administering an antagonist of the vitronectin receptor.

Additionally, a recent study referred to an $\alpha_v\beta_3$ antagonist as promoting tumor regression by inducing apoptosis of angiogenic blood vessels [P. C. Brooks, et al., *Cell*, 1994, 79: 1157–1164]. Similarly a murine monoclonal antibody LM609 developed to the vitronectin receptor reported in International Patent Publication No. WO89/05155, published Jun. 15, 1995, was referred to as useful in the inhibition of tumor growth. See, also, D. A. Cheresh et al, *Cell*, 1989, 57:59–69.

While passive immunotherapy employing monoclonal antibodies from a heterologous species (e.g., murine) has been suggested as a useful mechanism for treating or preventing various diseases or disorders, one alternative to reduce the risk of an undesirable immune response on the part of the patient directed against the foreign antibody is to employ "humanized" antibodies. These antibodies are substantially of human origin, with only the Complementarity Determining Regions (CDRs) and certain framework residues that influence CDR conformation being of non-human origin. Particularly useful examples of this approach for the treatment of some disorders are disclosed in PCT Application PCT/GB91/01554, Publication No. WO 92/04381 and PCT Application PCT/GB93/00725, Publication No. WO93/20210.

A second and more preferred approach is to employ fully human mAbs. Unfortunately, there have been few successes in producing human monoclonal antibodies through classic hybridoma technology. Indeed, acceptable human fusion partners have not been identified and murine myeloma fusion partners do not work well with human cells, yielding unstable and low producing hybridoma lines.

Novel human mAbs or humanized antibodies are particularly useful alone or in combination with existing molecules to form immunotherapeutic compositions. There remains a need in the art for fully human mAbs to vitronectin receptor $\alpha_v\beta_3$ or humanized antibodies thereto which can selectively block the integrin $\alpha_v\beta_3$ and display a long serum half-life.

SUMMARY OF THE INVENTION

In one aspect, this invention relates to a novel humanized monoclonal antibody directed against $\alpha_v\beta_3$ and functional fragments thereof. This humanized antibody is specifically reactive with the human $\alpha_v\beta_3$ (vitronectin receptor) and capable of neutralizing its function.

In a related aspect, the present invention provides modifications to neutralizing Fab fragments or F(ab')$_2$ fragments specific for the human $\alpha_v\beta_3$ receptor produced by random combinatorial cloning of human antibody sequences and isolated from a filamentous phage Fab display library.

In still another aspect, there is provided a reshaped human antibody containing human heavy and light chain constant regions from a first human donor and heavy and light chain variable regions or the CDRs thereof derived from human neutralizing monoclonal antibodies for the human $\alpha_v\beta_3$ receptor derived from a second human donor.

In yet another aspect, the present invention provides a pharmaceutical composition which contains one (or more) altered antibodies and a pharmaceutically acceptable carrier.

In a further aspect, the present invention provides a method for passive immunotherapy of a disorder mediated by $\alpha_v\beta_3$ receptor, such as restenosis, cancer metastasis, rheumatoid arthritis or atherosclerosis, among others, in a human by administering to said human an effective amount of the pharmaceutical composition of the invention for the prophylactic or therapeutic treatment of the disorder.

In still another aspect, the invention provides a method for treating a disease which is mediated by the vitronectin receptor in a human, by administering to the human an immunotherapeutically effective amount of the antibody of the invention, followed by administering to said human a therapeutically effective amount of a small chemical molecule which is an antagonist of the receptor.

In yet another aspect, the present invention provides methods for, and components useful in, the recombinant production of humanized and altered antibodies (e.g., engineered antibodies, CDRs, Fab or F(ab')$_2$ fragments, or analogs thereof) which are derived from neutralizing monoclonal antibodies (mAbs) for the human $\alpha_v\beta_3$ receptor. These components include isolated nucleic acid sequences encoding same, recombinant plasmids containing the nucleic acid sequences under the control of selected regulatory sequences which are capable of directing the expression thereof in host cells (preferably mammalian) transfected with the recombinant plasmids. The production method involves culturing a transfected host cell line of the present invention under conditions such that the human or altered antibody is expressed in said cells and isolating the expressed product therefrom.

Yet another aspect of the invention is a method to diagnose the presence of the human $\alpha_v\beta_3$ receptor overexpression in a human which comprises contacting a biopsy sample with the antibodies and altered antibodies of the instant invention and assaying for the occurrence of binding between said antibody (or altered antibody) and the human $\alpha_v\beta_3$ receptor.

In yet another embodiment of the invention is a pharmaceutical composition comprising at least one dose of an immunotherapeutically effective amount of the antibodies of this invention in combination with at least one additional monoclonal or altered antibody. A particularly desirable composition comprises as the additional antibody, an anti-human $\alpha_v\beta_3$ receptor antibody distinguished from the subject antibody by virtue of being reactive with a different epitope of the human $\alpha_v\beta_3$ receptor.

Other aspects and advantages of the present invention are described further in the detailed description and the preferred embodiments thereof.

DETAILED DESCRIPTION OF THE INVENTION

Figure 1:
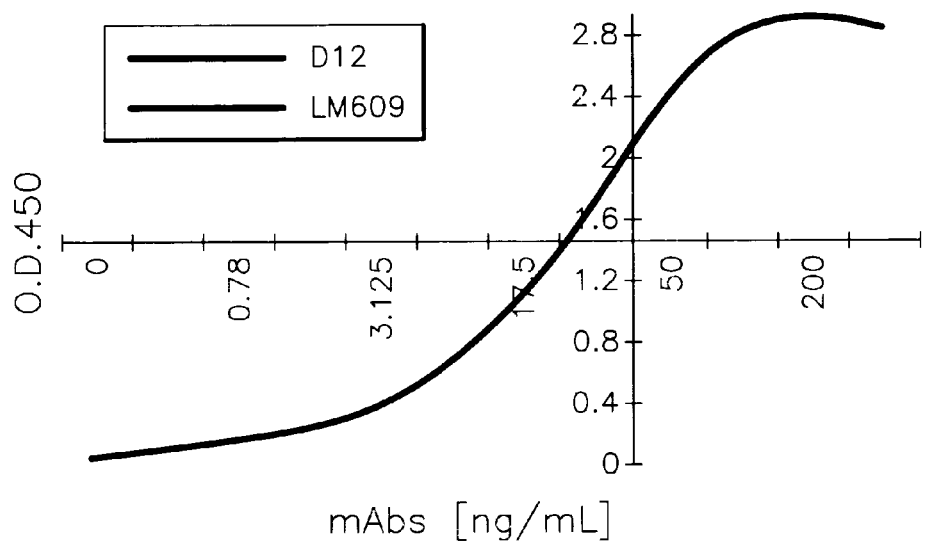
FIG. 1 is a graph illustrating the binding of mAbs to human $\alpha_v\beta_3$ receptor via ELISA as described in Example 3 for D12 and LM609.

The present invention provides useful antibodies, including monoclonal, recombinant and synthetic antibodies (and fragments thereof) reactive with the human vitronectin $\alpha_v\beta_3$ receptor, isolated nucleic acids encoding same and various means for their recombinant production as well as therapeutic, prophylactic and diagnostic uses of such antibodies and fragments thereof.

The antibodies of this invention inhibit the binding of vitronectin and other ligands to the vitronectin ($\alpha_v\beta_3$) receptor. These antibodies can selectively block the integrin $\alpha_v\beta_3$ and display a long serum half-life in vivo in animal models (e.g., about 21 days). They display additional functions such as complement fixation. Specifically, the antibodies including the murine monoclonal D12 and the humanized antibody HuD12, which specifically neutralize $\alpha_v\beta_3$, are desirable for use as acute and subacute therapeutic reagents for the treatment of the disorders mediated by the vitronectin receptor. Inhibition of the vitronectin receptor by the antibodies of this invention permits therapeutic treatment or prophylaxis of diseases such as restenosis and angiogenesis.

I. Sequence ID Nos.

Sequence ID Nos. 1 and 2 are the heavy chain variable region DNA and amino acid sequences, respectively, of murine mAb D12. The CDRs are located at AA residues 31–35, nucleotides 91–105; AA 50–66, nucleotides 148–198; and AA 99–106, nucleotides 295–318 of SEQ ID NOS: 1 and 2.

Sequence ID Nos. 6 and 7 are the light chain DNA and amino acid sequences, respectively, of the murine mAb D12. The CDRs are located at AA24–34, nucleotides 70–102; AA50–56, nucleotides 148–168; and AA89–97, nucleotides 265–291 of SEQ ID NOS: 6 and 7.

Sequence ID No. 3 is the heavy chain variable region amino acid sequence of the human VH subgroup I consensus sequence, in which the CDRs are located at AA31–35; AA49–64; and AA97–104. SEQ ID NO: 8 is the light chain amino acid sequence of the human V kappa subgroup III consensus sequence, in which the CDRs are located at AA24–35, AA51–57 and AA90–99.

Sequence ID Nos. 4 and 5 are the synthetic heavy chain variable region DNA and amino acid sequences, respectively, of the consensus humanized heavy chain D12HZHC1-0. The CDRs are located at AA31–35, nucleotides 91–115; AA50–66, nucleotides 148–198; and AA99–106, nucleotides 295–318. Preferred murine framework residues retained in the synthetic heavy chain are the AA residues 28, 48, 67, 68, 70, 72 and 74.

Sequence ID Nos. 9 and 10 are the synthetic light chain DNA and amino acid sequences, respectively, of the consensus, synthetic, humanized light chain D12HZLC-1-0. The CDRs are located at AA24–34, nucleotides 70–102; AA50–56, nucleotides 148–168; and AA89–97, nucleotides 265–291. Preferred murine framework residues are amino acid residues 1, 49 and 60.

Sequence ID Nos. 11 and 12 are the DNA and amino acid sequences, respectively, of the region of the murine D12 heavy chain variable region being altered. Sequence ID Nos. 13 and 14 are the DNA and amino acid sequences, respectively, of the region of the murine D12 light chain variable region being altered, including the first five amino acids of the human kappa constant region.

Sequence ID No. 15 is the amino acid sequence of the modified human REI kappa chain framework.

Sequence ID Nos. 16 and 17 are the DNA and amino acid sequences, respectively, of the Jk gene and its gene product.

Sequence ID Nos. 18 and 19 are the DNA and amino acid sequences, respectively, of the CAMPATH signal sequence.

Sequence ID Nos. 20 and 21 are the DNA and amino acid sequences, respectively, of the synthetic humanized kappa chain based on a modified human REI kappa chain framework.

Sequence ID Nos. 22–25, 30–31, 36–39, and 44–45 are primer sequences used in Examples 13 and 14.

Sequence ID Nos. 26–29, 32–35, and 40–43 are synthetic oligos used in Examples 13 and 14.

II. Definitions.

As used in this specification and the claims, the following terms are defined as follows:

The phrase "disorders mediated by the $\alpha_v\beta_3$ receptor", includes, but is not limited to, cardiovascular disorders or angiogenic-related disorders, such as angiogenesis associated with diabetic retinopathy, atherosclerosis and restenosis, chronic inflammatory disorders, macular degeneration, diabetic retinopathy, and cancer, e.g., solid tumor metastasis, and diseases wherein bone resorption is associated with pathology such as osteoporosis. The antibodies of this invention are useful also as anti-metastatic and antitumor agents.

"Altered antibody" refers to a protein encoded by an immunoglobulin coding region altered from its natural form, which may be obtained by expression in a selected host cell. Such altered antibodies are engineered antibodies (e.g., chimeric, humanized, or reshaped or immunologically edited human antibodies) or fragments thereof lacking all or part of an immunoglobulin constant region, e.g., $F_v$, Fab, or $F(ab')_2$ and the like.

"Altered immunoglobulin coding region" refers to a nucleic acid sequence encoding an altered antibody of the invention or a fragment thereof "Reshaped human antibody" refers to an altered antibody in which minimally at least one CDR from a first human monoclonal donor antibody is substituted for a CDR in a second human acceptor antibody. Preferably all six CDRs are replaced. More preferably an entire antigen combining region, for example, an Fv, Fab or $F(ab')_2$, from a first human donor monoclonal antibody is substituted for the corresponding region in a second human acceptor monoclonal antibody. Most preferably the Fab region from a first human donor is operatively linked to the appropriate constant regions of a second human acceptor antibody to form a full length monoclonal antibody.

"First immunoglobulin partner" refers to a nucleic acid sequence encoding a human framework or human immunoglobulin variable region in which the native (or naturally-occurring) CDR-encoding regions are replaced by the CDR-encoding regions of a donor human antibody. The human variable region can be an immunoglobulin heavy chain, a light chain (or both chains), an analog or functional fragment thereof. Such CDR regions, located within the variable region of antibodies (immunoglobulins) can be determined by known methods in the art. For example, Kabat el al, *Sequences of Proteins of Immunological Interest*, 4th Ed., U.S. Department of Health and Human Services, National Institutes of Health (1987) disclose rules for locating CDRs. In addition, computer programs are known which are useful for identifying CDR regions/structures.

"Second fusion partner" refers to another nucleotide sequence encoding a protein or peptide to which the first immunoglobulin partner is fused in frame or by means of an optional conventional linker sequence (i.e., operatively linked). Preferably the fusion partner is an immunoglobulin gene and when so, it is referred to as a "second immunoglobulin partner". The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or $F(ab')_2$ (i.e., a discrete part of an appropriate human constant region or framework region). A second fusion partner may also comprise a sequence encoding an integral membrane protein exposed on the outer surface of a host cell, e.g., as part of a phage display library, or a sequence encoding a protein for analytical or diagnostic detection, e.g., horseradish peroxidase, $\beta$-galactosidase, etc.

The terms Fv, Fc, Fd, Fab, or $F(ab')_2$ are used with their standard meanings [see, e.g., Harlow et al, *Antibodies A Laboratory Manual*, Cold Spring Harbor Laboratory, (1988)].

As used herein, an "engineered antibody" describes a type of altered antibody, i.e., a full-length synthetic antibody (e.g., a chimeric, humanized, reshaped, or immunologically edited human antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chain) derived from a donor antibody in association with light and heavy chain constant regions derived from an acceptor antibody from a heterologous species.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity [see, e.g., Queen et al., 1991, *Proc. Natl. Acad. Sci. USA*, 86:10029–10032 and Hodgson et al., 1991, *Bio/Technology*, 9:421].

An "immunologically edited antibody" refers to a type of engineered antibody in which changes are made in donor and/or acceptor sequences to edit regions involving cloning artifacts, germ line enhancements, etc. aimed at reducing the likelihood of an immunological response to the antibody on the part of a patient being treated with the edited antibody.

The term "donor antibody" refers to an antibody (monoclonal or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a neutralizing murine monoclonal anti-$\alpha_v\beta_3$ antibody, designated as D12. D12 is defined as having the variable heavy chain and variable light chain amino acid sequences shown in SEQ ID NOS: 2 and 7, respectively.

The term "acceptor antibody" refers to an antibody (monoclonal or recombinant) from a source genetically unrelated to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"Consensus VH" or "Consensus VK" regions refer to amino acid sequences which can function in a manner similar to the framework regions of the acceptor antibody, but are selected by conventional computer techniques. Briefly, provided with a given VH or VK amino acid sequence, the human VH and VK sequences closest to the given sequence are assembled to identify the closest antibody subgroup. Once the subgroup is selected, all human antibodies from that subgroup are compared and a consensus sequence of the VH and VK chains are prepared. The consensus sequences are used to generate a desirable synthetic framework region for the humanized antibody.

"CDRs" are the complementarity determining region amino acid sequences of an antibody. CDRs are the hypervariable regions of immunoglobulin heavy and light chains. See, e.g., Kabat et al, *Sequences of Proteins of Immunological Interest,* 4th Ed., U.S. Department of Health and Human Services, National Institutes of Health (1987). There are three heavy chain CDRs and three light chain CDRs (or CDR regions) in the variable portions of an immunoglobulin. Thus, "CDRs" as used herein refer to all three heavy chain CDRs, or all three light chain CDRs (or both all heavy and all light chain CDRs, if appropriate). CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By "sharing the antigen binding specificity or neutralizing ability" is meant, for example, that although mAb D12 may be characterized by a certain level of antigen affinity, a CDR encoded by a nucleic acid sequence of mAb D12 in an appropriate structural environment may have a lower or higher affinity. It is expected that CDRs of mAb D12 in such environments will nevertheless recognize the same epitope(s) as does the intact mAb D12.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be a chemical modification or substitution onto an amino acid or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Where in this text, protein and/or DNA sequences are defined by their percent homologies or identities to identified sequences, the algorithms used to calculate the percent homologies or percent identities include the following: the Smith-Waterman algorithm [J. F. Collins et al, 1988, *Comput. Appl. Biosci.*, 4:67–72; J. F. Collins et al, Molecular Sequence Comparison and Alignment, (M. J. Bishop et al, eds.) in Practical Approach Series: Nucleic Acid and Protein Sequence Analysis XVIII, IRL Press: Oxford, England, UK (1987) pp.417], and the BLAST and FASTA programs [E. G. Shpaer et al, 1996, *Genomics* 38:179–191]. These references are incorporated herein by reference.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore (Pharmacia) system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

III. Anti-$\alpha_v\beta_3$ Murine Monoclonal Antibodies

For use in constructing the humanized antibodies, fragments and fusion proteins of this invention, a non-human species may be employed to generate a desirable immunoglobulin upon presentment with the human placental $\alpha_v\beta_3$ receptor as antigen. Conventional hybridoma techniques are employed to provide a hybridoma cell line secreting a non-human monoclonal antibody (mAb) to the $\alpha_v\beta_3$ receptor. As one example, the production of murine mAb D12, and other murine anti-$\alpha_v\beta_3$ mAbs is described in detail in Example 2 below. For ease of discussion below, the term D12 may refer to the D12 mAb or any of the other mAbs of Example 2.

D12 is a desirable donor antibody for use in developing a chimeric or humanized antibody of this invention. The characteristics of the neutralizing murine mAb D12 obtained as described in Example 2 include an antigen binding specificity for human $\alpha_v\beta_3$ and characteristics listed in Table I below. The isotype of the mAb D12 of Example 2 is IgG$_1$, and it has an affinity of between about 1 and 3 nM, depending on the assay employed. The antibody recognizes the heterodimeric α and β epitope of $α_vβ_3$ and does not recognize either α or β subunits individually. The binding is illustrated by binding and functional activity (neutralization) in the in vitro assays of Examples 3–12 below).

Given the sequences provided, i.e. the light chain variable region of D12 [SEQ ID NOS: 6 and 7] and the heavy chain variable region of D12 [SEQ ID NOS: 1 and 2], one of skill in the art could obtain the remaining portions of the heavy chain using, for example, polymerase chain reaction, and thus obtain a complete mAb molecule. Alternatively, a D12 molecule could be constructed using techniques analogous to those described below for the synthetic and recombinant mAbs of the invention and employing other murine IgG subtype heavy chains.

Other anti-$α_vβ_3$ antibodies may be developed by screening hybridomas or combinatorial libraries, or antibody phage displays [W. D. Huse et al., 1988, Science, 15 246:1275–1281] using the murine mAb described herein and its $α_vβ_3$ epitope. A collection of antibodies, including hybridoma products or antibodies derived from any species immunoglobulin repertoire may be screened in a conventional competition assay, such as described in Examples 5, 8 and 9 below, with one or more epitopes described herein. Thus, the invention may provide an antibody, other than D12, which is capable of binding to and neutralizing the $α_vβ_3$ receptor. Other mAbs generated against a desired $α_vβ_3$ epitope and produced by conventional techniques, include without limitation, genes encoding murine mAbs, human mAbs, and combinatorial antibodies.

This invention is not limited to the use of the D12 mAb or its hypervariable sequences. It is anticipated that any appropriate $α_vβ_3$ neutralizing antibodies and corresponding anti-$α_vβ_3$ CDRs described in the art may be substituted therefor. Wherever in the following description the donor antibody is identified as D12, this designation is made for illustration and simplicity of description only.

IV. Combinatorial Cloning to Obtain Human Antibodies

As mentioned above, a number of problems have hampered the direct application of the hybridoma technology of G. Kohler and C. Milstein, 1975, Nature, 256: 495–497 to the generation and isolation of human monoclonal antibodies. Among these are a lack of suitable fusion partner myeloma cell lines used to form hybridoma cell lines as well as the poor stability of such hybridomas even when formed. Therefore, the molecular biological approach of combinatorial cloning is preferred.

Combinatorial cloning is disclosed generally in PCT Publication No. WO90/14430. Simply stated, the goal of combinatorial cloning is to transfer to a population of bacterial cells the immunological genetic capacity of a human cell, tissue or organ. It is preferred to employ cells, tissues or organs which are immunocompetent. Particularly useful sources include, without limitation, spleen, thymus, lymph nodes, bone marrow, tonsil and peripheral blood lymphocytes. The cells may be optionally stimulated with the human $α_vβ_3$ receptor in vitro, or selected from donors which are known to have produced an immune response or donors who are HIV+ but asymptomatic.

The genetic information (i.e., the human antibodies produced in the tissues in response to stimulation by $α_vβ_3$ as antigen) isolated from the donor cells can be in the form of DNA or RNA and is conveniently amplified by PCR or similar techniques. When isolated as RNA the genetic information is preferably converted into cDNA by reverse transcription prior to amplification. The amplification can be generalized or more specifically tailored. For example, by a careful selection of PCR primer sequences, selective amplification of immunoglobulin genes or subsets within that class of genes can be achieved.

Once the component gene sequences are obtained, in this case the genes encoding the variable regions of the various heavy and light antibody chains, the light and heavy chain genes are associated in random combinations to form a random combinatorial library. Various recombinant DNA vector systems have been described to facilitate combinatorial cloning [see, e.g., PCT Publication No. WO90/14430 supra, Scott and Smith, 1990, Science, 249:386–406 or U.S. Pat. No. 5,223,409]. Having generated the combinatorial library, the products can, after expression, be conveniently screened by biopanning with the human $α_vβ_3$ receptor or, if necessary, by epitope blocked biopanning as described in more detail below.

Initially it is generally preferred to use Fab fragments of mAbs, such as D12, for combinatorial cloning and screening and then to convert the Fabs to full length mAbs after selection of the desired candidate molecules. However, single chain antibodies can also be used for cloning and screening.

V. Antibody Fragments

The present invention contemplates the use of Fab fragments or F(ab')$_2$ fragments to derived full-length mAbs directed against the human $α_vβ_3$ receptor. Although these fragments may be independently useful as protective and therapeutic agents in vivo against conditions mediated by the human $α_vβ_3$ receptor or in vitro as part of a diagnostic for a disease mediated by the human $α_vβ_3$ receptor, they are employed herein as a component of a reshaped human antibody. A Fab fragment contains the entire light chain and amino terminal portion of the heavy chain; and an F(ab')$_2$ fragment is the fragment formed by two Fab fragments bound by additional disulfide bonds. Human $α_vβ_3$ receptor binding monoclonal antibodies of the present invention provide sources of Fab fragments and F(ab')$_2$ fragments, which latter fragments can be obtained from combinatorial phage library [see, e.g., Winter et al., 1994, Ann. Rev. Immunol., 12:433–455 or Barbas et al., 1992, Proc. Natl. Acad. Sci. USA, 89:10164–10168 which are both hereby incorporated by reference in their entireties]. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

VI. Anti-human $α_vβ_3$ Antibody Amino Acid and Nucleotide Sequences of Interest The mAb D12 or other antibodies described herein may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

As one example, the present invention thus provides variable light chain [SEQ ID NOS: 6 and 7] and variable heavy chain sequences [SEQ ID NOS: 1 and 2] from the anti-human $α_vβ_3$ mAb D12 and sequences derived therefrom.

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions can be used to create restriction enzyme sites which would facilitate insertion of mutagenized CDR (and/or framework) regions. These CDR-encoding regions may be used in the construction of reshaped human antibodies of this invention.

Taking into account the degeneracy of the genetic code, various coding sequences may be constructed which encode the variable heavy and light chain amino acid sequences, and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies, or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Such sequences include all nucleic acid sequences which by virtue of the redundancy of the genetic code are capable of encoding the same amino acid sequences as provided in SEQ ID NOS: 2 and 7. An exemplary humanized light chain variable DNA sequence is illustrated in SEQ ID NO: 9. An exemplary humanized heavy chain variable DNA sequence is illustrated in SEQ ID NO: 4. These heavy chain and the light chain variable regions have three CDR sequences described in detail in the murine sequences of SEQ ID NOS: 1, 2, 6 and 7.

Other useful DNA sequences encompassed by this invention include those sequences which hybridize under stringent hybridization conditions [see, e.g., T. Maniatis et al., 1982, *Molecular Cloning (A Laboratory Manual)*, Cold Spring Harbor Laboratory pages 387 to 389] to the DNA sequences encoding the light and heavy chain variable regions of SEQ ID NOS: 1 and 6 (also including SEQ ID NOS: 4 and 9 for the synthetic human sequences) and which retain the antigen binding properties of those antibodies. An example of one such stringent hybridization condition is hybridization at 4×SSC at 65° C., followed by a washing in 0.1×SSC at 65° C. for an hour. Alternatively an exemplary stringent hybridization condition is in 50% formamide, 4×SSC at 42° C. Preferably, these hybridizing DNA sequences are at least about 18 nucleotides in length, i.e., about the size of a CDR. Still other useful sequences are those DNA sequences which are about 80% to about 99% homologous or identical with the DNA sequences of SEQ ID NOS: 1, 4, 6, 9, 11, 13, and 20 herein, according to any of the algorithms listed above, which encode sequences sharing the biological activities or functions of SEQ ID NOS: 2, 5, 7, 10, 12, 14 and 21.

VII. Altered Immunoglobulin Coding Regions and Altered Antibodies

Altered immunoglobulin coding regions encode altered antibodies which include engineered antibodies such as chimeric antibodies, humanized, reshaped and immunologically edited human antibodies. A desired altered immunoglobulin coding region contains CDR-encoding regions in the form of Fab regions that encode peptides having the antigen specificity of the anti-human $\alpha_v\beta_3$ antibody, preferably a high affinity antibody such as provided by the present invention, inserted into an acceptor immunoglobulin partner.

When the acceptor is an immunoglobulin partner, as defined above, it includes a sequence encoding a second antibody region of interest, for example an Fc region. Immunoglobulin partners may also include sequences encoding another immunoglobulin to which the light or heavy chain constant region is fused in frame or by means of a linker sequence. Engineered antibodies directed against functional fragments or analogs of the human $\alpha_v\beta_3$ protein may be designed to elicit enhanced binding with the same antibody.

The immunoglobulin partner may also be associated with effector agents as defined above, including non-protein carrier molecules, to which the immunoglobulin partner may be operatively linked by conventional means.

Fusion or linkage between the immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified to enhance expression. For example the reshaped human antibody having the signal sequence and CDRs derived from the mAb D12 heavy chain sequence, may have the original signal peptide replaced with another signal sequence, such as the Campath leader sequence [Page, M. J. et al., 1991, *BioTechnology*, 9:64–68; SEQ ID NOS: 18 and 19].

An exemplary altered antibody, a reshaped human antibody, contains a variable heavy and the entire light chain peptide or protein sequence having the antigen specificity of mAb D12 fused to the constant heavy regions $C_{H-1}$–$C_{H-3}$ derived from a second human antibody.

In still a further embodiment, the engineered antibody of the invention may have attached to it an additional agent. For example, the procedure of recombinant DNA technology may be used to produce an engineered antibody of the invention in which the Fc fragment or CH2 CH3 domain of a complete antibody molecule has been replaced by an enzyme or other detectable molecule (i.e., a polypeptide effector or reporter molecule).

Another desirable protein of this invention may comprise a complete antibody molecule, having full length heavy and light chains, or any discrete fragment thereof, such as the Fab or F(ab')$_2$ fragments, a heavy chain dimer, or any minimal recombinant fragments thereof such as an $F_v$ or a single-chain antibody (SCA) or any other molecule with the same specificity as the selected donor mAb D12. Such protein may be used in the form of an altered antibody, or may be used in its unfused form.

Whenever the immunoglobulin partner is derived from an antibody different from the donor antibody, e.g., any isotype or class of immunoglobulin framework or constant regions, or is selected by a computer program as a consensus sequence, as defined above, an engineered antibody results.

Engineered antibodies can comprise immunoglobulin (Ig) constant regions and variable framework regions from one source, e.g., the acceptor antibody or consensus sequences, and one or more (preferably all) CDRs from the donor antibody, e.g., the anti-human $\alpha_v\beta_3$ antibody described herein. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity or to reduce potential immunogenicity.

Such engineered antibodies are designed to employ one (or both) of the variable heavy and/or light chains of the human $\alpha_v\beta_3$ mAb (optionally modified as described) or one or more of the below-identified heavy or light chain CDRs. The engineered antibodies of the invention are neutralizing, i.e., they desirably inhibit ligand binding to the vitronectin receptor in vitro and in vivo in animal models of diseases mediated by the $\alpha_v\beta_3$ receptor, e.g., restenosis.

Such engineered antibodies may include a reshaped human antibody containing the human heavy and light chain constant regions fused to the human $\alpha_v\beta_3$ antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. Alternatively, a consensus sequence formed by all known human sequences in the database of a subgroup closest to that of the donor antibody may be used to supply the framework regions. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA and IgE. The Fc domains are not limited to native sequences, but include mutant variants known in the art that alter function. For example, mutations have been described in the Fc domains of certain IgG antibodies that reduce Fc-mediated complement and Fc receptor binding [see, e.g., A. R. Duncan et al., 1988, *Nature*, 332:563–564; A. R. Duncan and G. Winter, 1988, *Nature*, 332:738–740; M.-L. Alegre et al., 1992, *J. Immunol.*, 148:3461–3468; M.-H. Tao et al., 1993, *J. Exp. Med.*, 178:661–667; V. Xu et al, 1994, *J. Biol. Chem.*, 269:3469–2374] and alter clearance rate [J.-K. Kim et al., 1994, *Eur. J. Immunol.*, 24:542–548] and reduce structural heterogeneity [S. Angal et al., 1993, *Mol. Immunol.*, 30:105–108]. Also, other modifications are possible such as oligomerization of the antibody by addition of the tailpiece segment of IgM and other mutations [R. I. F. Smith and S. L. Morrison, 1994, *Biotechnology*, 12:683–688; R. I. F. Smith et al., 1995, *J. Immunol.*, 154: 2226–2236] or addition of the tailpiece segment of IgA [I. Kariv et al., 1996, *J. Immunol.*, 157: 29–38]. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

One example of a particularly desirable altered antibody is a humanized antibody containing all or a portion of the variable domain amino acid sequences of D12 and some portions of the donor antibody framework regions, or CDRs therefrom inserted onto the framework regions of a selected human antibody. This humanized antibody is directed against human $\alpha_v\beta_3$ receptor. Suitably, in these humanized antibodies one, two or preferably three CDRs from the D12 antibody heavy chain and/or light chain variable regions are inserted into the framework regions of a selected human antibody or consensus sequence, replacing the native CDRs of that latter antibody or consensus sequence.

Preferably, in a humanized antibody, the variable domains in both human heavy and light chains have been engineered by one or more CDR replacements. It is possible to use all six CDRs, or various combinations of less than the six CDRs. For example, it is possible to replace the CDRs only in the human heavy chain, using as light chain the unmodified light chain from the human acceptor antibody. Still alternatively, a compatible light chain may be selected from another human antibody by recourse to the conventional antibody databases. The remainder of the engineered antibody may be derived from any suitable acceptor human immunoglobulin.

The altered antibody thus preferably has the structure of a natural human antibody or a fragment thereof, and possesses the combination of properties required for effective therapeutic use, e.g., treatment of human $\alpha_v\beta_3$ receptor-mediated diseases in man, or for diagnostic uses.

It will be understood by those skilled in the art that an altered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both. Particularly preferred is the immunological editing of such reconstructed sequences as illustrated in the examples herein.

In addition, the variable or constant region may be altered to enhance or decrease selective properties of the molecules of the instant invention. Such properties can include, for example, dimerization, binding to Fc receptors, or the ability to bind and activate complement [see, e.g., Angal et al., 1993, *Mol. Immunol.*, 30:105–108; Xu et al., 1994, *J. Biol. Chem.*, 269:3469–3474; Winter et al., EP 307,434-B].

Such antibodies are useful in the prevention and treatment of human $\alpha_v\beta_3$ receptor-mediated disorders, as discussed below.

VIII. Production of Altered Antibodies and Engineered Antibodies

The resulting reshaped and engineered human, humanized and chimeric antibodies of this invention can be expressed in recombinant host cells, e.g., COS, CHO or myeloma cells, by resort to recombinant DNA technology using genetic engineering techniques. The same or similar techniques may also be employed to generate other embodiments of this invention.

Briefly described, a conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The production of the antibody which includes the association of both the recombinant heavy chain and light chain is measured in the culture by an appropriate assay, such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the conventional pUC series of cloning vectors, may be used. One vector used is pUC19, which is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vectors. Preferred vectors include for example plasmids pCD or pCN. The vectors also contain selected regulatory sequences (such as CMV promoters) which direct the replication and expression of heterologous DNA sequences in selected host cells. These vectors contain the above described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a polyadenylation (poly A) signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3), and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., 1989, *Molecular Cloning (A Laboratory Manual)*, 2nd edit., Cold Spring Harbor Laboratory (New York).

Bacterial cells may prove useful as host cells suitable for the expression of the recombinant Fabs of the present invention [see, e.g., Plückthun, A., 1992, *Immunol. Rev.*, 130:151–188]. The tendency of proteins expressed in bacterial cells to be in an unfolded or improperly folded form or in a non-glycosylated form does not pose as great a concern as Fabs are not normally glycosylated and can be engineered for exported expression thereby reducing the high concentration that facilitates misfolding. Nevertheless, any recombinant Fab produced in a bacterial cell would have to be screened for retention of antigen binding ability. If the molecule expressed by the bacterial cell was produced and exported in a properly folded form, that bacterial cell would be a desirable host. For example, various strains of *E. coli* used for expression are well-known as host cells in the field of biotechnology. Various strains of *B. subtilis, Streptomyces,* other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., 1986, *Genetic Engineering*, 8:277–298 and references cited therein.

The general methods by which the vectors of the invention may be constructed, the transfection methods required to produce the host cells of the invention, and culture methods necessary to produce the altered antibody of the invention from such host cells are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of reshaped antibodies may utilize expression in a transgenic animal, such as described in U.S. Pat. No. 4,873,316, incorporated herein by reference.

Once expressed by the desired method, the engineered antibody is then examined for in vitro activity by use of an appropriate assay. Presently conventional ELISA assay formats are employed to assess qualitative and quantitative binding of the altered antibody to the human $\alpha_v\beta_3$ receptor. See, Example 3 below. Additionally, other in vitro assays (such as Example 12) and in vivo animal (such as Example 15) models may also be used to verify neutralizing efficacy prior to subsequent human clinical studies performed to evaluate the persistence of the altered antibody in the body despite the usual clearance mechanisms.

As one specific example of the production processes described above, a humanized D12 antibody is generated and expressed as described in detail in Example 13 below.

IX. Therapeutic/Prophylactic Uses

This invention also relates to a method of treating humans experiencing symptoms related to human $\alpha_v\beta_3$ receptor-mediated disease, which comprises administering an effective dose of antibodies including one or more of the altered antibodies described herein or fragments thereof. The antibodies of this invention are useful for treating diseases wherein the underlying pathology is attributable to ligand which interacts with the vitronectin receptor. For instance, these antibodies are useful as antitumor, anti-angiogenic, anti-inflammatory and anti-metastatic agents, and are particularly useful in the treatment of atherosclerosis, restenosis, cancer metastasis, rheumatoid arthritis, diabetic retinopathy and macular degeneration.

Similarly, these antibodies are useful for treatment of conditions wherein loss of the bone matrix creates pathology. Thus, the instant antibodies are useful for the treatment of osteoporosis, hyperparathyroidism, Paget's disease, hypercalcemia of malignancy, osteolytic lesions produced by bone metastasis, bone loss due to immobilization or sex hormone deficiency.

The altered antibodies and mAbs of this invention, which are specific against the $\alpha_v\beta_3$ integrin receptor are useful therapeutics due to their "long half-life" (~21 days) and additional effector functions (e.g., Complement fixation). The $\alpha_v\beta_3$ receptor expressed on blood vessels provides an easy access with mAbs. In addition, these antibodies of the present invention are useful in targeted drug delivery in which case they could enhance drug delivery (i.e., as immuno-conjugates, or immuno-liposomes). Restenosis may be blocked either by blocking neointima formation; or by promoting remodeling. The vascular smooth muscle cell (VSMC) migration is mediated via the $\alpha_v\beta_3$ receptor which is upregulated following vascular injury (documented by immnunohistology) and osteopontin, a ligand of $\alpha_v\beta_3$, is also upregulated following vascular injury. Therefore, the antagonists of $\alpha_v\beta_3$ receptor, i.e., the antibodies and altered antibodies described herein can block neointima formation and enhance favorable remodeling of the vessel.

Angiogenesis is the process of new blood vessel formation from a pre-existing blood vessel in response to angiogenic stimuli. The antibodies and compositions of this invention may also be used to treat diseases having angiogenic components, including, without limitation, solid tumors, cancer metastasis, rheumatoid arthritis, chronic inflammatory diseases, atherosclerosis, diabetic retinopathy and macular degeneration. In cancer, treating angiogenesis represents targeting (treating) the host itself which is independent of the cancer cell phenotype. The compositions of this invention which are antagonists of $\alpha_v\beta_3$ receptor have efficacy against diseases with angiogenic components because $\alpha_v\beta_3$ is upregulated in the neovasculature during angiogenesis. An anti-$\alpha_v\beta_3$ mAb inhibits angiogenesis in the chick chorioallantoic membrane (CAM), promotes apoptosis in endothelial cells and inhibits tumor growth in the human-SCID mouse model. Inhibition of $\alpha_v\beta_3$ prevents growth of neovasculature (no effect on mature vessels).

Thus, the therapeutic response induced by the use of the molecules of this invention is produced by the binding to the vitronectin receptor $\alpha_v\beta_3$ and thus subsequently blocking disease progression. Thus, the molecules of the present invention, when in preparations and formulations appropriate for therapeutic use, are highly desirable for those persons experiencing disorders mediated by the human $\alpha_v\beta_3$ receptor. For example, longer treatments may be desirable when treating chronic diseases or the like. The dose and duration of treatment relates to the relative duration of the molecules of the present invention in the human circulation, and can be adjusted by one of skill in the art depending upon the condition being treated and the general health of the patient.

The altered antibodies, antibodies and fragments thereof of this invention may also be used alone or in conjunction with other antibodies, particularly human or humanized or human antibodies reactive with other epitopes on the vitronectin receptor as prophylactic agents.

The mode of administration of the therapeutic and prophylactic agents of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously, or intranasally.

Therapeutic and prophylactic agents of the invention may be prepared as pharmaceutical compositions containing an effective amount of the altered antibody of the invention as an active ingredient in a pharmaceutically acceptable carrier. An aqueous suspension or solution containing the antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc.

The concentration of the antibody of the invention in such pharmaceutical formulation can vary widely, i.e., from less than about 0.5%, usually at or at least about 1%, to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg of an engineered antibody of the invention. Desirably the compositions may contain about 50 ng to about 80 mg of antibody, or more preferably, about 5 mg to about 75 mg of antibody according to this invention. Similarly, a pharmaceutical composition of the invention for intravenous infusion could be made up to contain about 250 ml of sterile Ringer's solution, and about 1 to about 75 and preferably 5 to about 50 mg/ml of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

It is preferred that the therapeutic and prophylactic agents of the invention, when in a pharmaceutical preparation, be present in unit dose forms. The appropriate therapeutically effective dose can be determined readily by those of skill in the art. To effectively treat an inflammatory disorder in a human or other animal, one dose of approximately 0.1 mg to approximately 20 mg per 70 kg body weight of a protein or an antibody of this invention should be administered parenterally, preferably i.v. or i.m. (intramuscularly). Such dose may, if necessary, be repeated at appropriate time intervals selected as appropriate by a physician.

The antibodies, altered antibodies or fragments thereof described herein can be lyophilized for storage and reconstituted in a suitable carrier prior to use. This technique has been shown to be effective with conventional immunoglobulins and art-known lyophilization and reconstitution techniques can be employed.

In still an alternative therapeutic regimen, the alter antibodies and monoclonal antibodies of this invention can be used in a combined therapy for the diseases described above with small molecule non-peptide antagonists of the vitronectin receptor. Such small molecule antagonists, the dosages and administration regimens are described in, e.g., International PCT patent publication No. WO96/00730, published Jan. 11, 1996 and International PCT patent publication No. WO96/00574, published Jan. 11, 1996, both incorporated by reference herein. Such combination therapy may involve administering an antibody of this invention to a patient for a short period, i.e., several months to six months, followed by chronic therapeutic treatment with the small molecule antagonists for a longer period of time. In another embodiment, this embodiment of a method of treatment may involve alternating treatment periods of administering immunotherapy with the antibodies of this invention followed by small non-peptide antagonist treatments. Such combined therapeutic methods would employ the same dosages described above for the immunotherapy and the dosages specified in the above-cited applications for the non-peptide therapies.

X. Diagnostic Uses

The altered antibodies and engineered antibodies of this invention may also be used in diagnostic regimens, such as for the determination of human $\alpha_v\beta_3$ receptor-mediated disorders or tracking progress of treatment of such disorders. As diagnostic reagents, these altered antibodies may be conventionally labeled for use in ELISAs and other conventional assay formats for the measurement of human $\alpha_v\beta_3$ receptor levels in serum, plasma or other appropriate tissue or the release by human cells in culture. The nature of the assay in which the altered antibodies are used are conventional and do not limit this disclosure.

The following examples illustrate various aspects of this invention including the construction of exemplary engineered antibodies and expression thereof in suitable vectors and host cells, and are not to be construed as limiting the scope of this invention. All amino acids are identified by conventional three letter or single letter codes. All necessary restriction enzymes, plasmids, and other reagents and materials were obtained from commercial sources unless otherwise indicated. All general cloning ligation and other recombinant DNA methodology were as performed in T. Maniatis et al. or Sambrook et al., both cited above.

EXAMPLE 1

Purification of $\alpha_v\beta_3$, $\alpha_v\beta_5$, and $\alpha_v\beta_1$ Receptors The human $\alpha_v\beta_3$ protein receptor and other protein receptors were purified from human placenta as follows. Placentas were frozen immediately after birth, then partially thawed and cut into small chunks which were ground to fine pieces using a commercial meat grinder. Usually five to ten placentas were ground at one time; the pieces were placed into 50 ml centrifuge tubes (6 tubes per placenta) and stored frozen at −20° C. until use.

An immunoaffinity column for each integrin was prepared using individual monoclonal antibodies. Anti-$\alpha_v\beta_3$ mAb (LM609) was purified from mouse ascites purchased from Chemicon International, Inc. (Temecula, Calif.). Monoclonal antibodies 23C6 or D12 were purified from hybridoma media. Anti-$\alpha_v\beta_5$ mAb (P1F6) and anti-$\alpha_v\beta_1$ mAb (mAb16) were purchased from Becton Dickinson. LM609 or 23C6 or D12 (50 mg), P1F6 (25 mg), and mAb16 (25 mg) were immobilized on AffiGel 10 (BioRad) at 5 mg of mAb/ml of resin following the manufacturer's instruction. In order to remove the nonspecific binding proteins, ~20 ml of AffiGel 10 was treated with 1 M Tris HCl pH 7.5 and packed in an Econo Column. The immobilized mAb's were packed in EconoColumn (BioRad), 10 ml column for LM609 or 23C6 or D12, 5 ml one for P1F6 and 5 ml one for mAb16. The columns were connected in tandem: the first column containing AffiGel 10 for nonspecific binding, the second column containing $\alpha_v\beta_3$ mAb, the third column containing $\alpha_v\beta_1$ mAb and the fourth column containing $\alpha_v\beta_5$ mAb. The columns were equilibrated with buffer T (50 mM TrisHCl, pH 7.5, 0.1 M NaCl, 2 mM CaCl, 1% octyl glucoside) in the coldroom.

The ground placenta (9 tubes) was partially thawed and dispersed thoroughly using spatula in buffer T+6% octyl glucoside (final concentration of OG was 3%). The mixture was stored for 5 hours or overnight at 4° C. The bulky solution was transferred to 250 ml centrifuge bottles and centrifuged at 13,000 rpm for one hour. The clear supernatant was transferred to 50 ml centrifuge tubes and centrifuged at 20,000 rpm for one hour. The clear supernatant was combined and loaded with the flow-rate of 30 ml/hour to the columns arranged and pre-equilibrated in buffer T in tandem mode as described above. At the end of loading, the columns were washed with >250 ml of buffer T. Individual columns were then separated and the bound integrins were eluted with 0.2 M acetic acid until pH of the eluate reached <3.0. The eluted integrin solutions were quickly neutralized to >pH 7.0 with 1M Trizma base. The column was also neutralized by washing with buffer T.

The eluted integrin solutions (~25 ml) were concentrated to ~1 ml using Aquaside III (Calbiochem) in a dialysis bag of 5000 cut off. The concentrated integrins were dialyzed overnight against buffer T. The final yield was approximately 1 mg for each integrin per placenta.

EXAMPLE 2

Generation of Murine Monoclonal Antibodies

Murine mAbs with anti-$\alpha_v\beta_3$ activity were generated by classical hybridoma technology according to Lane el al, 1986, *Methods in Enzymol.*, 121:183. Generally, 20–50 µg of $\alpha_v\beta_3$ receptor was administered ip, sc, and iv to two Balb/c mice. Sera from the immunized animals were tested for their anti-$\alpha_v\beta_3$ binding and neutralizing activity in assays of Examples 3, 4 and 5 below. Mouse spleen from mice showing positive sera was fused with a mouse myeloma cell SP2 according to the procedures of Lane et al, cited above. Seventeen resulting hybridoma cell lines, secreting potential anti-human $\alpha_v\beta_3$ protein antibodies were obtained. These anti-$\alpha_v\beta_3$ mAbs were generated and isolated from culture by conventional methods and tested in assays of the following examples.

Table I is a summary of much of the early data collected from Examples 3–12 below on the murine mAb LM609 of the prior art and murine mAbs of this invention. The data showed that mAb D12 was a mAb with favorable activity profile. The mAb D12 that functioned adequately in these tests was then selected for humanization as described in Example 13, and further tested in animals models of Examples 16 and 17. The D12 mAb cross-reacts with rabbit, therefore only rabbit models of restenosis, angiogenesis or atherosclerosis are applicable for testing efficacy.

TABLE I

| mAbs: Profiles | LM609 | D12 | 293 93 | 293 601 | 294 7,50 | 23 346 |
|---|---|---|---|---|---|---|
| $\alpha_v\beta_3$ ELISA | + | + | + | + | + | + |
| $\alpha_5\beta_1$ and $\alpha_v\beta_5$ ELISA | − | − | − | − | − | − |
| $\alpha$IIb$\beta$3 ELISA | − | − | − | − | − | + |
| Specificity | $\alpha_v\beta_3$ | $\alpha_v\beta_3$ | $\alpha_v\beta_3$ | $\alpha_v\beta_3$ | $\alpha_v\beta_3$ | $\beta_3$ |
| Neutralization | 3+ | 3+ | 3+ | 3+ | + | +/− |
| Immuno o-histology | 3+ | 3+ | 3+ | + | 3+ | 2+ |
| Inhib. Adhes. HEK293 ($V_n$) | + | + | + | + | + | −* |
| Echistatin binding HEK293 | 3+ | 3+ | 3+ | 2+ | N.D. | − |
| FLOW Hu-SMC/R-SMC | +/+ | +/+ | +/+ | +/+ | +/+ | +/+ +rat/mouse |
| Inhib (%) R-SMC (50 mg/ml) | 43 | 66 | 83 | 33 | 60 | 75 |

EXAMPLE 3

ELISA Binding Assay with $\alpha_v\beta_3$

Binding of the various antibody constructs to purified human placenta $\alpha_v\beta_3$ receptor protein as antigen (receptor either bound to the plate or to the beads via biotin-avidin) was measured in a standard solid phase ELISA.

Antigen diluted in 0.1 M $CO_3$ pH 9.2 was adsorbed onto polystyrene round-bottom microplates (Dynatech, Immunolon II) for 18 hours. Wells were then washed one time with phosphate buffered saline (PBS) containing 0.05% Tween 20. Antibodies (50 μl/well) were diluted to varying concentrations in PBS/0.05% Tween 20 and added to the antigen coated wells for two hours at room temperature. Plates were washed four times with PBS containing 0.05% Tween 20, using a Titertek 320 microplate washer, followed by addition of HRP-anti-mouse IgG (100 μl/well) diluted 1:10,000.

After washing five times, o-phenylenediamine dihydrochloride (OPD) (1 mg/ml) was added and plates were incubated an additional 10 minutes. The reaction was stopped by addition of 0.1M NaF and absorbance read at 450 nm using a Dynatech MR 7000 ELISA reader.

EXAMPLE 4

ELISA Binding Assays With $\alpha_v\beta_5$, $\alpha_5\beta_1$ and $\alpha$IIb$\beta$3

MAbs positive in the assay of Example 3 were screened using the same protocols except that the antigen was another human receptor, $\alpha_v\beta_5$, $\alpha_5\beta_1$ or $\alpha_{IIb}\beta_3$. These assays were run to determine selectivity for the heterodimeric antigen $\alpha_v\beta_3$, as opposed to selectivity for an $\alpha$ or a $\beta$ subunit only. The results of these assays are reported in Table I below for all mAbs of Example 2 and for LM609.

EXAMPLE 5

Neutralization ELISA Assay

Vitronectin receptor $\alpha_v\beta_3$ (0.2 ug/well), purified from human placenta, was added to 96-well Elisa plates (Corning, New York, N.Y.). The plates were incubated overnight at 4° C. At the time of experiment, the wells were aspirated and incubated in 0.1 ml of Buffer A (50 mM Tris, 100 mM NaCl, 1 mM $CaCl_2$, 1 mM $MgCl_2$, 1 mM $MnCl_2$, pH 7.4) containing 3% bovine serum albumen (BSA) for 1 hour at room temperature to block nonspecific binding. After aspirating the blocking solution, various concentrations of mAbs were added to the wells and followed by the addition of 5 nM biotinylated fibrinogen in 0.1 ml of Buffer A containing 0.1% BSA. The plates were incubated for 1 hour at room temperature.

Following the incubation the wells were aspirated completely and washed twice with 100 μl of binding buffer. Bound fibrinogen was quantitated by addition of 0.1 ml of an anti-biotin antibody conjugated to alkaline phosphatase (1:2000 dilution, Sigma), followed by washing twice with binding buffer and the addition of 100 μl of the substrate p-nitrophenyl phosphate prepared daily according to the manufacturer's instructions (alkaline phosphate substrate kit, Bio-Rad). The kinetics of color development were followed using a microtiter plate reader.

This assay detected inhibition of binding between purified $\alpha_v\beta_3$ receptor and its ligand, fibronectin. The results of these assays are reported in Table I above for all mAbs of Example 2 and for LM609.

EXAMPLE 6

Flow Cytometry

A. Characterization of the Murine mAbs

To characterize several of the murine mAbs obtained as described above with the known murine mAb LM609, this assay was performed to detect binding to the native cell surface receptor and species cross-reactivity.

Briefly described, cells are washed in 10 ml cold PBS and resuspended in cold PBS to give between $1\times10^7$ to $2\times10^7$ cells/ml. Aliquots of 0.1 ml/well are added to 96 well "V" bottom plate. Then, 25 μl of primary antibody is added. The plates are shaken for five minutes, and then incubated on ice for 25 minutes. The plates are centrifuged for five minutes and flicked. Thereafter the contents of each well is resuspended in 50 μl cold PBS, and again centrifuged and flicked. The wash is repeated and the contents resuspended to 50 μl cold PBS. Fluorescein isothiocyanate (FITC)-labelled secondary antibody (50 μl) is added to each well. The plates are shaken for five minutes, and incubated on ice in the dark for 20 minutes. One μl of propidium iodide (PI) (1 mg/ml)/PBS is added to a final concentration of 10 μg/ml (1 μg in 0.1 ml). Incubation is continued for five minutes, followed by centrifuging and washing twice in cold PBS.

Cells are resuspended to 0.1 ml cold PBS, and transferred to 12×75 clear Falcoln tubes. Volume is adjusted to 1 ml, and cells are held cold in the dark until read by FLOW.

The secondary antibody:Goat Anti-Mouse IgG,M,A is labelled with FITC 1:25/PBS-0.2% BSA-0.1% $NaN_3$ (Sigma F1010 lot #045H8822) and held cold in the dark until read by FLOW.

The results of these assays are reported in Table I above for all mAbs of Example 2 and for LM609. Flow cytometry using human and rabbit smooth muscle cells (SMC) indicated that both mAbs LM609 and D12 have great capability to bind to a native receptor on the cell surface.

B. Characterization of the Murine and Humanized Antibodies

Figure 8:
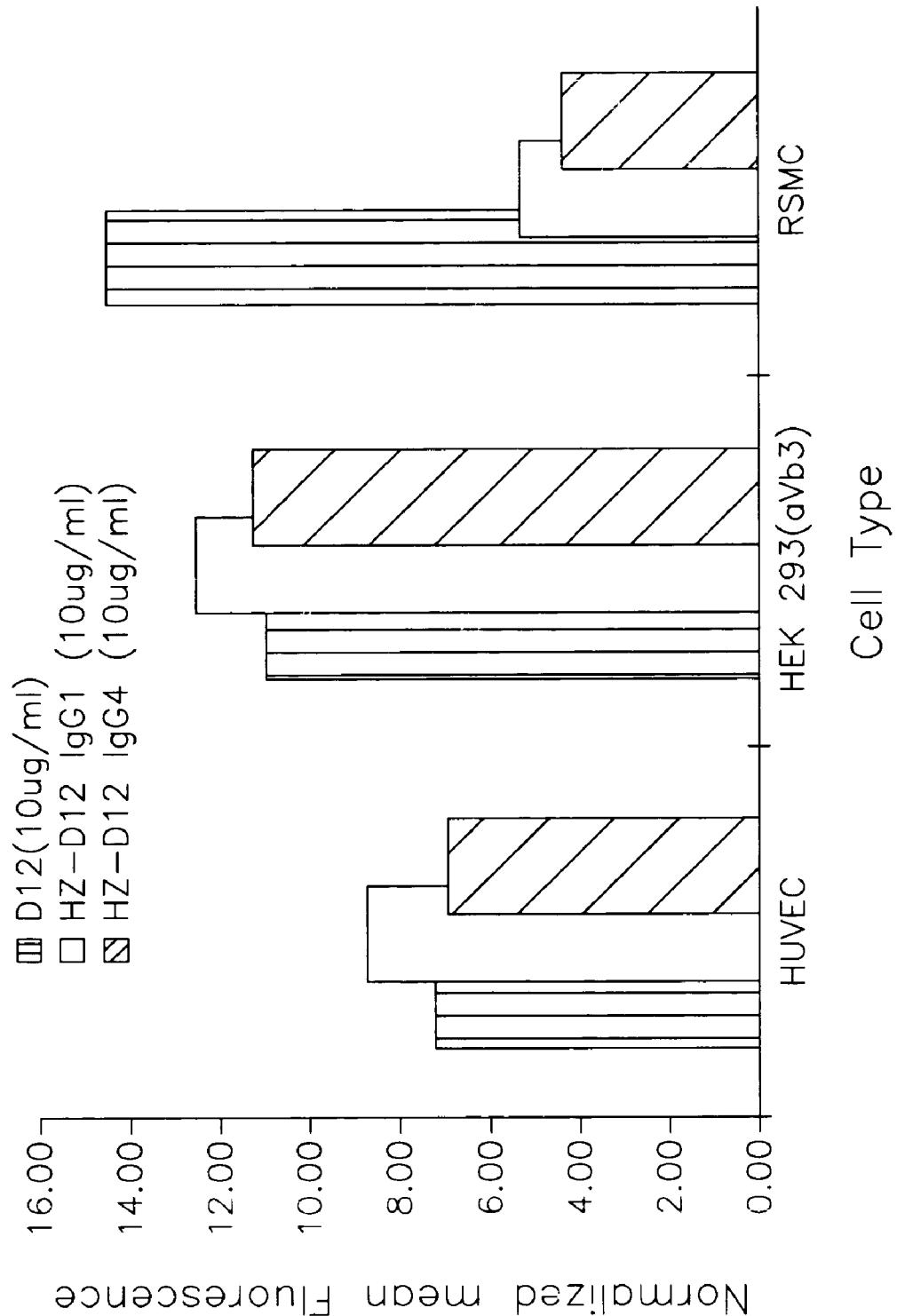
FIG. 8 is a bar graph illustrating the flow cytometry results of the murine and humanized D12 antibodies against two human cell types and a rabbit cell type. See, Example 6.

The murine and humanized mabs of Example 13 were tested by flow cytometry using methods as substantially set forth above for their capability to detect $\alpha_v\beta_3$ receptor on viable human umbilical vein endothelial cells (HUVEC), human embryonic kidney cells (HEK 293) and rabbit smooth muscle cells (RSMC) cells. FIG. 8 indicates that the affinities of the murine D12 mAb, and the humanized HZ-D12 IgG$_1$ and HZ-D12 IgG$_4$ (see Example 13) are comparable on the human cells (HUVEC and HEK 293). The humanized mAbs lost some of their affinity when tested on the rabbit SMC. This result is expected as D12 mAbs have a 10 fold higher affinity against human $\alpha_v\beta_3$ than against the rabbit receptor.

EXAMPLE 7

Immunohistology

A. Immunohistology was performed on tissues expressing high levels of receptors, such as human osteoclastoma. Data from immunohistology (human osteoclastoma) showed that D12 may have slightly better detection capability to LM609. See Table I.

B. Target Validation

Subsequent immunohistology on other human tumor tissue as indicated in Table II showed that human tumors express $\alpha_v\beta_3$ receptor and therefor represent good targets for immune therapy with the humanized antibodies and other compositions of this invention. The D12 mAbs, including the humanized mAbs of Example 13, also tested positive on a human blood vessel. In Table II below, (+) indicates the detection of a ligand, e.g., the $\alpha_{v3}$ receptor for the mAb in the tissue; (–) indicates the absence of such a ligand.

TABLE II

| Human Tissue: | D12 mAb |
|---|---|
| osteoclastoma | +++ |
| normal skin (adult) | – |
| normal skin (close to melanoma tumor) | + |
| metastatic melanoma (TM) | +++ |
| melanoma cells (from tumor biopsy) | + |
| lymph node met (melanoma) (LNM) | +++ |
| metastatic melanoma (MM) | +/– |
| lung carcinoma (LR) | + |
| colorectal carcinoma | + |
| metastatic squamous tumor (MSC) | +++ |

EXAMPLE 8

BIAcore to Determine Affinity to the Receptor

A. Affinity Measurements for D12 and LM609

A BIAcore analysis (Pharmacia) was performed to measure binding affinity of mAbs D12 and LM609 (6nM) with immobilized $\alpha_v\beta_3$. The interactions of $\alpha_v\beta_3$ with D12 and LM609 were studied using BIAcore technology by immobilization of the receptor onto the sensor surface, and passing solutions of the mAbs over this surface. Descriptions of the instrumentation and sensor surfaces are described in [Brigham-Burke, Edwards and O'Shannessy, 1992, Analytical Biochem., 205:125–131]. The $\alpha_v\beta_3$ was immobilized by inserting the $\alpha_v\beta_3$ into a phospholipid vesicle and producing a hybrid bilayer membrane on a hydrophobic sensor surface. A more complete description of generation of hybrid bilayer membranes on BIAcore sensor surfaces is provided in Plant et al, 1995, Analyt. Biochem., 226:342–348. Samples of the mAbs were passed over this surface and the rates at which they bound and then dissociated from the surface were measured and analyzed using software provided with the instrument.

Figure 3:
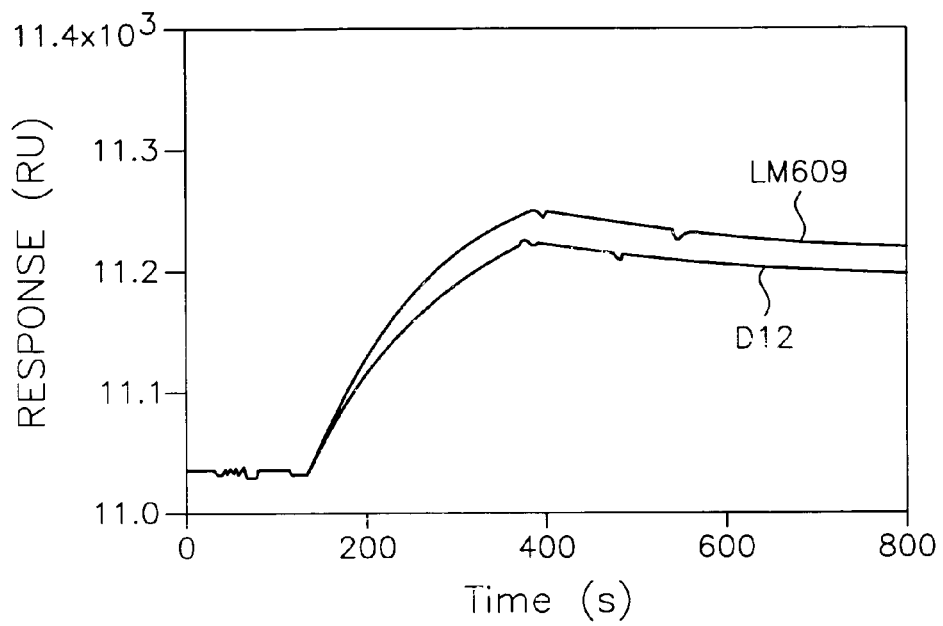
FIG. 3 is a graph representing BIAcore data of D12 and LM609 (6 nM) binding with immobilized $\alpha_v\beta_3$, as described in Example 8.

FIG. 3 is a graph representing this data. Kinetic rate constants and calculated affinity constant ($K_D$) were derived from the analysis of three mAb concentrations (100, 25, 6 nM) performed in triplicate. The BIAcore data showed that the binding affinity ($K_D$) of D12 is 530 pM, which is comparable to 460 pM for LM609.

B. Affinity Measurements of Murine and Humanized mAbs

The murine D12 mAb has been humanized as described in detail in Examples 13 and 14 below. Humanized IgG$_1$ and IgG$_4$ HZ-D12 antibodies were generated as described in those examples.

Affinity measurements of murine D12 and the humanized mAbs were determined by BIAcore as described in part A above. The results reported in Table III indicate that the class switching of the humanized D12 mAbs had no measurable effect. The data indicate that upon humanization the affinity of the D12 has not been altered.

TABLE III

| mAb | calc. $K_D$ (nM) anti-$\alpha_v\beta_3$ |
|---|---|
| murine D12 | 1.3 |
| HZD12-IgG$_1$ | 1.0 |
| HZD12-IgG$_4$ | 1.1 |
| murine LM609 | 3.8 |

EXAMPLE 9

Binding and Competition with LM609 and Backup mAbs

A. LM609 was labeled (ORIGEN-TAG labeled). ORIGEN is an electrochemiluminescent moiety which can detect and quantitate by the well-known ORIGEN analysis. The anti-$\alpha_v\beta_3$ binding of LM609 was competed with other anti-$\alpha_v\beta_3$ mAbs of Example 2. This assay tests antibodies for the ability to prevent 1 µg/ml of LM609 from binding 1 µg/ml biotin-labeled $\alpha_v\beta_3$ in ORIGEN. The antibodies studied are D12 and the backup antibodies listed in Table 1.

Figure 2:
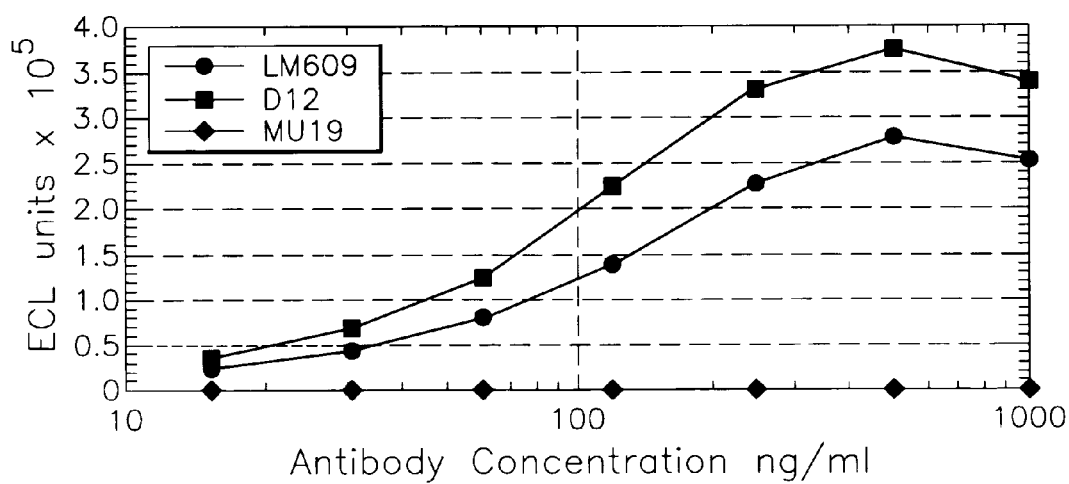
FIG. 2 is a graph illustrating the binding of mAbs to $\alpha_v\beta_3$ receptor via an Origen label for D12 and LM609 and MU19 as control (see Example 9).

The results displayed in FIG. 2 illustrate the binding of mAbs to $\alpha_v\beta_3$ receptor via Origen for D12 and LM609, with Mu19 (an IgG$_{2a}$) as a control. These results showed that 1 µg/ml of tag-labeled LM609 shows 90% inhibition when competed with 10 µg/ml and 70% inhibition when competed with 1 µg/ml of D12 mAbs. These results suggest that D12 mAb binds to a similar epitope as LM609 on the receptor. This data indicate that D12 has a higher binding activity than LM609.

Figure 4:
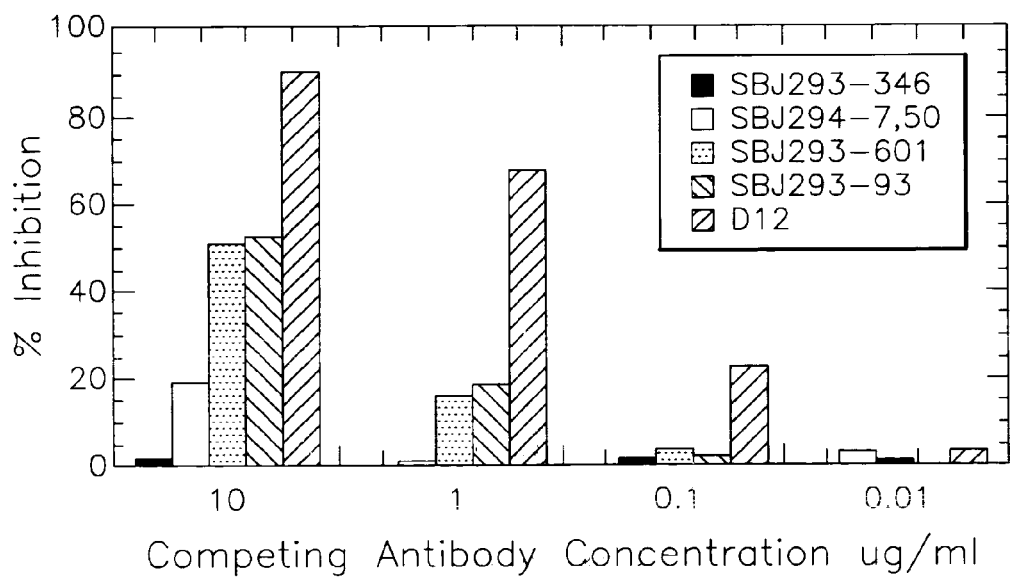
FIG. 4 is a graph illustrating the characteristics of antibodies (D12 and the backup antibodies listed in Table I) for the ability to prevent 1 μg/ml of LM609 from binding 1 μg/ml $\alpha_v\beta_3$ in an ORIGEN label experiment. See Example 9.

B. The results of FIG. 4 illustrate comparative binding of the D12 and other mAbs of Example 2 in competition with LM609 for µg/ml $\alpha_v\beta_3$ in Origen. The antibodies listed in Table I showed that the binding epitope on the $\alpha_v\beta_3$ receptor is different from LM609 and D12. For example, mAb 346 inhibited SMC and showed good flow and immunohistology profiles (Table I), but does not compete with LM609.

Figure 6:
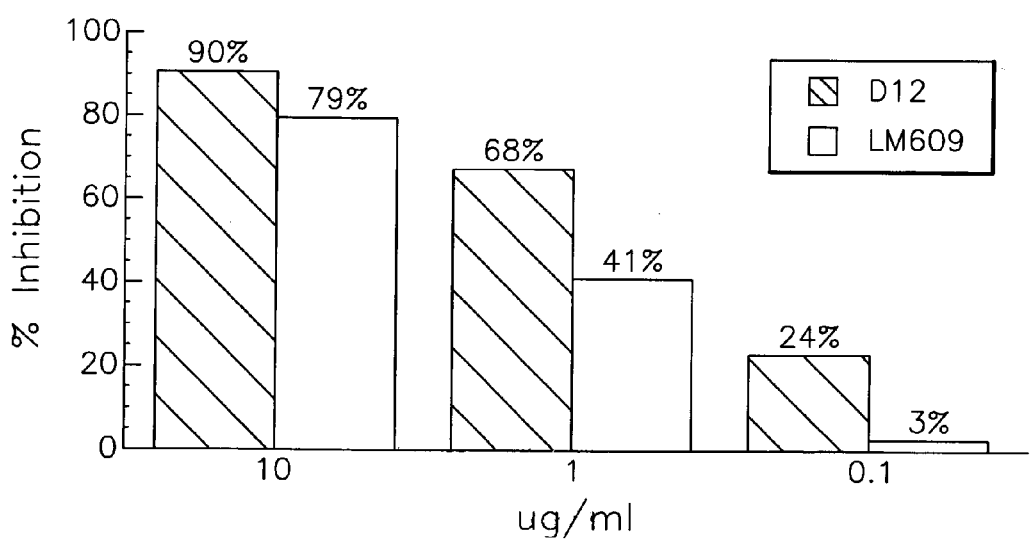
FIG. 6 is a bar graph illustrating the inhibition of binding of 1 μg/ml LM609 to 1 μg/ml $\alpha_v\beta_3$ by preincubating with LM609 or D12.

C. FIG. 6 also demonstrates the binding affinities of these antibodies. Twenty-five microliters of $\alpha_v\beta_3$-biotin and 25 µl of unlabeled LM609 or D12 were mixed for 30 minutes. Twenty-five µl of Tag-LM609 was added for 30 minutes, followed by 50 µl of 0.6 ng/ml streptavidin magnetic beads for 15 minutes. The mixture was then read on an ORIGEN analyzer. The results are depicted in the bar graph of FIG. 6. D12 showed a consistently higher binding affinity for the receptor than LM609.

Figure 7:
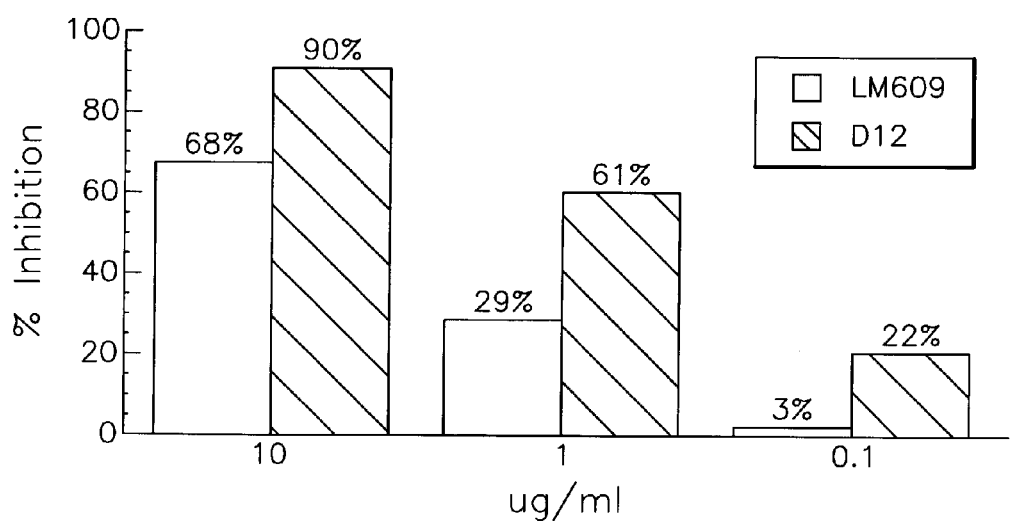
FIG. 7 is a bar graph illustrating the inhibition of binding of 1 μg/ml D12 to 1 μg/ml $\alpha_v\beta_3$ by preincubating with LM609 or D12.

D. FIG. 7 illustrates another assay in which inhibition of binding of 1 µg/ml D12 to 1 µg/ml $\alpha_v\beta_3$ receptor was determined by preincubating with LM609 or D12. Again D12 was shown to have higher binding affinity than LM609.

EXAMPLE 10

Vascular Smooth Muscle Cell (SMC) Migration Assay

Smooth muscle cell (SMC) migration from the media into the wound area to initiate growth of the neointima is an essential remodeling response following vascular injury. Inhibition of SMC migration attenuates neointima formation. Vascular SMC migration is mediated via the human $\alpha_v\beta_3$ receptor, which is expressed in VSMC and upregulated following vascular injury. Osteopontin, a ligand of the human $\alpha_v\beta_3$ receptor, is upregulated following angioplasty and promotes VSMC migration via the integrin. This experiment was performed to demonstrate the ability of an antibody to human $\alpha_v\beta_3$ to inhibit VSMC migration in vitro.

Human or rabbit aortic smooth muscle cells were used. Cell migration was monitored in a Transwell cell culture chamber by using a polycarbonate membrane with pores of 8 um (Costar). The lower surface of the filter was coated with vitronectin or osteopontin. Cells were suspended in Difco's minimal essential medium (DMEM) supplemented with 0.2% BSA at a concentration of 2.5–5.0×10$^6$ cells/mL, and were pretreated with test antibody at various concentrations for 20 minutes at 20° C. The solvent alone was used as control. 0.2 mL of the cell suspension was placed in the upper compartment of the chamber. The lower compartment contained 0.6 mL of DMEM supplemented with 0.2% BSA. Incubation was carried out at 37° C. in an atmosphere of 95% air/5% $CO_2$ for 24 hours.

After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Inhibition of SMC migration (human and rabbit) showed that LM609 is more potent than D12. See Table I.

Figure 9:
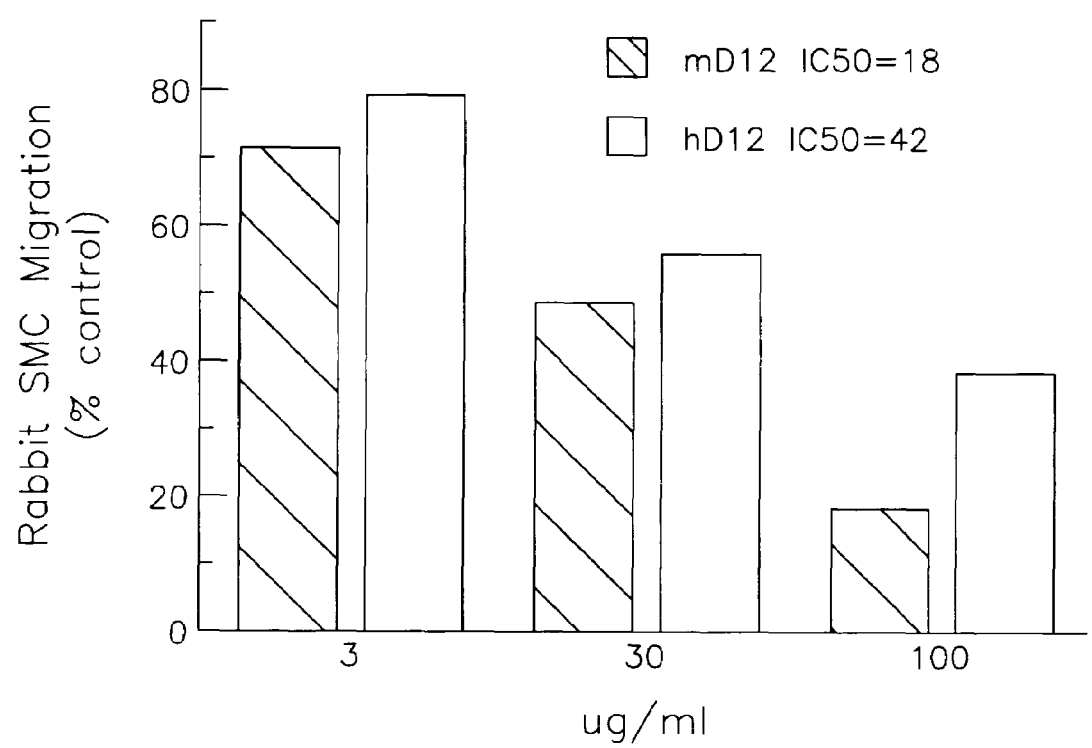
FIG. 9 is a bar graph illustrated the inhibition of rabbit smooth muscle cells in the assay of Example 10 by the murine D12 mAb (black bars) and the humanized HZ D12 IgG$_1$ (white bars).

In a subsequent assay, and prior to testing the efficacy of the murine mAb D12 and the humanized HZ-D12 (IgG$_1$) of Example 13 in the rabbit model of restenosis, these mAbs were again tested for inhibition of rabbit SMC migration. The results illustrated in FIG. 9 indicate that the murine D12 has higher potency in comparison to its humanized HZ-D12 (IgG$_1$) version.

EXAMPLE 11

HEK293 Cell Adhesion to Determine Inhibition of Adhesion

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum (FBS), 1% glutamine and 1% Penicillin-Streptomycin.

A 3.2 kb EcoRI-KpnI fragment of the $\alpha_v$ subunit and a 2.4 kb XbaI-XhoI fragment of the β3 subunit were inserted into the EcoRI-EcoRV cloning sites of the pCDN vector which contains a CMV promoter and a G418 selectable marker by blunt end ligation. For stable expression, 80×10$^6$ HEK 293 cells were electrotransformed with $\alpha_v\beta_3$ constructs (20 µg DNA of each subunit) using a Gene Pulser [P. Hensley et al., 1994, J. Biol. Chem., 269:23949–23958] and plated in 100 mm plates (5×10$^5$ cells/plate). After 48 hours, the growth medium was supplemented with 450 µg/ml Geneticin (G418 Sulfate, GIBCO-BRL, Bethesda, Md.). The cells were maintained in selection medium until the colonies were large enough to be assayed.

Corning 96-well ELISA plates were precoated overnight at 4° C. with 0.1 ml of human vitronectin (0.2 µg/ml in RPMI medium). At the time of the experiment, the plates were washed once with RPMI medium and blocked with 3.5% BSA in RPMI medium for 1 hour at room temperature. Transfected 293 cells were resuspended in RPMI medium, supplemented with 20 mM Hepes, pH 7.4 and 0.1% BSA at a density of 0.5×10$^6$ cells/ml. 0.1 ml of cell suspension was added to each well and incubated for 1 hour at 37° C., in the presence or absence of various $\alpha_v\beta_3$ antagonists. Following incubation, 0.025 ml of a 10% formaldehyde solution, pH 7.4, was added and the cells were fixed at room temperature for 10 minutes. The plates were washed 3 times and 0.2 ml of RPMI medium and the adherent cells were stained with 0.1 ml of 0.5% toluidine blue for 20 minutes at room temperature.

Excess stain was removed by extensive washing with deionized water. The toluidine blue incorporated into cells was eluted by the addition of 0.1 ml of 50% ethanol containing 50 mM HCl. Cell adhesion was quantitated at an optical density of 600 nm on a microtiter plate reader (Titertek Multiskan MC, Sterling, Va.).

Figure 5:
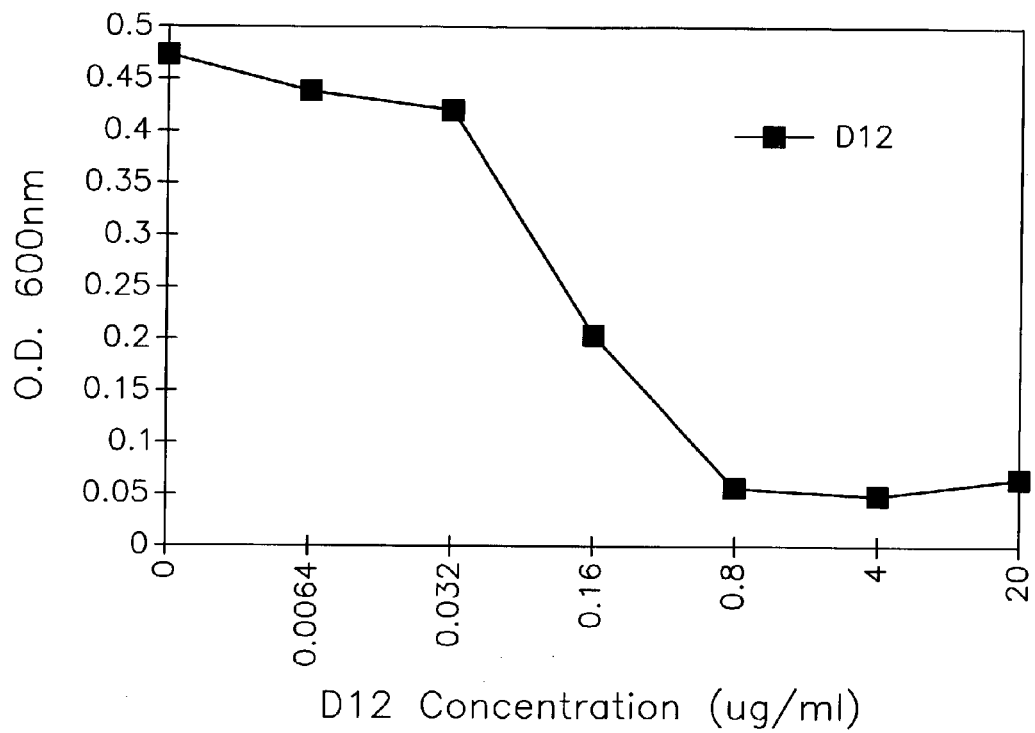
FIG. 5 is a graph illustrating the effect of humanized D12 concentration in the HEK293 Cell Adhesion Assay.

The neutralization of receptor inhibition of cell adhesion showed that D12, other back-up MABS of Example 2, and LM609 inhibit cell adhesion (see Table I and FIG. 5).

EXAMPLE 12

In Vivo Chick Embryo Chorio-allantoic Membrane (CAM) Assay for Angiogenesis

The chick embryo chorioallantoic membrane (CAM) assay was used to assess the role of $\alpha_v\beta_3$ antagonists on angiogenesis. The human $\alpha_v\beta_3$ protein is expressed and upregulated in the vasculature during angiogenesis. Blockade of the human $\alpha_v\beta_3$ receptor would inhibit endothelial cell (EC) migration, a key step in the angiogenic process and promotes EC apoptosis in neovessels without affecting mature blood vessels. LM609 or D12 inhibits angiogenesis induced by β-fibroblast growth factor (β-FGF) or spontaneously on the CAM of growing embryo. The key features in the procedure for the CAM assay are described below:

The Cam assay is performed with the CAM of 10 day old fertilized chick eggs. 5 mm diameter Whatman #1 filters are soaked in a 3 mg/ml cortisone solution (made in 95% ethanol), and air dried. Cortisone is used to decrease the inflammatory response to the filters. Filters are saturated in 1–6 ug/ml solution of B-FGF to stimulate angiogenesis (Hepes buffered saline solution (HBSS) is used as a buffer control) and placed on an avascular zone in the CAM.

LM609 or D12 (~100 ug) are applied in a volume of <20 μl to the filter discs on days 0, 1, 2 and 3 after β-FGF stimulation. On day 4 CAMs are dissected out and angiogenesis is quantitated by counting the number of vessel bifurcations under the filter, by using a stereomicroscope.

This assay demonstrates a positive correlation between the binding affinity to the receptor and inhibition of EC migration. This assay, while quite difficult to perform, showed that the human $\alpha_v\beta_3$ receptor plays a role in angiogenesis. The anti-$\alpha_v\beta_3$ antibodies of this invention are shown to inhibit β-FGF induced angiogenesis in this assay. See Table I.

EXAMPLE 13

Generating Humanized D12

A. Generating Heavy and Light Chain Variable Regions

A humanization strategy was adopted to obtain a maximally humanized mAb that retained full antigen binding avidity. The cDNA of the variable heavy chain (VH) and variable light chain (VK) of murine mAb D12 were cloned and sequenced. The sequence of VHD12 is shown in SEQ ID NOS: 1 and 2, with the CDRs identified as described and the sequence of VKD12 is shown in SEQ ID NOS: 6 and 7 with the CDRs identified.

Following cDNA cloning and sequence analysis, VH D12 and VK D12 were found to be most similar to Kabat VH subgroup I [SEQ ID NO: 3] and Kabat VK subgroup III [SEQ ID NO: 8], respectively. Humanized VH and VL regions were synthesized by combining the framework regions of the human V region consensus sequences together with the CDR regions of D12.

Molecular modeling of D12 using known crystal structures reveals certain VH and VL framework residues that can make contact with CDR loops, and thereby influence their conformation. Such framework residues can therefore directly contribute to the formation of a particular antigen specificity. Seven such murine VH framework residues and three murine VK framework residues were introduced into the human consensus framework regions, resulting in D12HZHC 1-0 [SEQ ID NO: 4 and 5] and D12HZLC 1-0 [SEQ ID NO: 9 and 10].

B. $\alpha_v\beta_3$ D12 MAb Heavy and Light Chain cDNA Sequence Analysis

Total RNA was purified by using TRizol Reagent (Life Technologies Cat. # 15596–026) according to manufacturer's protocol. RNA was precipitated with isopropanol and dissolved in diethylpyrocarbonate (DEPC) treated water. Poly A+ RNA was isolated using the Poly-A Quik mRNA Isolation Kit. (Stratagene Cat. # 200349) according to manufacturer's protocol.

Ten aliquots of 100 ng of RNA were reverse transcribed with a RT-PCR kit per the manufacturer's instructions (Boehringer Mannheim Cat. No. 1483-188) using a dT oligo for priming. For the heavy chain, PCR amplifications of 5 RNA/DNA hybrids were carried out for 25 cycles using a mouse IgG$_1$ hinge primer 5' TCT-TGT-CCA-CCT-TGG-TGC-TGC-TG 3' [SEQ ID NO: 22] and a heavy chain degenerate primer based on the N-terminal protein sequence 5' (G/C)(A/T)(G/A)-GT (C/T)-CA(G/A)-CT(G/T/C)-CA(A/G)-CA 3' [SEQ ID NO: 23].

Similarly, for the light chain, PCR amplifications of five RNA/DNA hybrids were carried out for 25 cycles using a mouse kappa primer 5' GCA-CCT-CCA-GAT-GTT-AAC-TGC 3' [SEQ ID NO: 24] and a primer based on the N-terminal protein sequence 5' GAC-ATT-GTG-CTG-ACT-CAG-TCT-CCA-GCC-A 3' [SEQ ID NO: 25]. The PCR DNA was analyzed on a 0.8% agarose gel. PCR inserts of the appropriate size, i.e., ~700 bp for the heavy chain and ~700 bp for the light chain were sequenced by a modification of the Sanger method.

The sequence of all 10 of the heavy and light chains were compared to generate a consensus D12 heavy chain variable region sequence, illustrated in SEQ ID NOS: 4 and 5 and consensus D12 light chain variable region sequence, illustrated in SEQ ID NOS: 9 and 10. In SEQ ID NOS: 4, 5, 9 and 10, the CDRs are identified; and the first 17 bases of DNA sequence for both the heavy and light chains are PCR primer generated. However, the translated protein sequence is exact.

C. Humanization of D12

The humanized D12 antibody as described herein consists of the synthetic, consensus heavy chain D12HZHC 1-0 [SEQ ID NOS: 4 and 5] and the synthetic, consensus light chain D12HZLC 1-0 [SEQ ID NOS: 9 and 10]. The antibody was constructed as follows.

i. Construction of D12HZHC 1-0

A synthetic variable region humanized heavy chain was designed using a consensus human subgroup I framework as defined by Kabat and the D12 murine heavy chain CDRs described previously. Seven murine framework amino acids substitutions which might influence CDR presentation were introduced at AA 28, 48, 67, 68, 70, 72 and 74 of SEQ ID NO: 5. Four overlapping synthetic oligonucleotides were generated which encode the following sequences:

SBA885:                                [SEQ ID NO: 26]
  TGCAACTAGT GCAGTCTGGA GCTGAGGTGA AGAAGCCTGG

GGCCTCAGTG AAGGTATCCT GCAAAGCTTC TGGTTATGCA

TTCACTAGCT ACAACATGTA;

SBA886:                                [SEQ ID NO: 27]
  TTGCCCTTGA ATTTCTGGTT GTAGAAAGTA TCACCATTGT

AAGGATCAAT ATATCCAATC CACTCTAGAC CCTGTCCAGG

GGCCTGCCGC ACCCAGTACA TGTTGTAGCT AGTG;

SBA887:                                [SEQ ID NO: 28]
  CTACAACCAG AAATTCAAGG GCAAGGCCAC ATTGACTGTC

GACAAGTCCA CCAGCACAGC CTACATGGAA CTCAGCAGCC

TGAGATCTGA GGACACTGCA GT; and

SBA888:                                [SEQ ID NO: 29]
  CCAGGGTACC TTGGCCCCAG TAAGCAAAAC TACCGTAGTT

CTGTCTTGCA CAGTAATAGA CTGCAGTGTC CTCAGATCTC

AGGCTGCTG.

When annealed and extended, the oligonucleotide sequences code for amino acids representing the region of the humanized heavy chain variable region being altered. SEQ ID NOS: 11 and 12, respectively, are the DNA and amino acid sequences of the intermediate of the synthetic heavy chain, i.e., representing the region of the D12 heavy chain variable region being altered. This synthetic gene was then amplified using PCR primers SBA883: TGCAAC-TAGT GCAGTCTGGA GCTGAGGT [SEQ ID NO: 30] and SBA884: CCAGGGTACC TTGGCCCCAG [SEQ ID NO: 31] and ligated into the pCR2000 vector (TA cloning kit, Invitrogen, Cat. No. K2000-01), and isolated after a SpeI, KpnI restriction digest.

This DNA fragment was ligated into the vector F9HZHC1-1 restriction digested with SpeI and KpnI. F9HZHC1-1 is a variant of plasmids pCDN [A. Nambi et al, 1994, Mol. Cell. Biochem., 131:75–85] and pPHZHC2-3pcd [International patent publication No. WO94/05690]. These pCD variant plasmid vectors contain, in general, a beta lactamase gene, an SV40 origin of replication, a cytomegalovirus promoter sequence, a selected humanized heavy chain, a polyA signal for bovine growth hormone, a beta-globin promoter, a dihydrofolate reductase gene and another BGH sequence polyA signal in a pUC19 background. F9HZHC1-1 further contains the Campath signal sequence including the first 3 amino acids of the mature heavy chain, the remainder of a human consensus framework 4, and the human IgG$_1$ constant region. The F9HZHC1-1 vector contains a single amino acid mutation of the pFHZHC2-3pcd vector in which the final residue of framework 2 (amino acid 49 reported in that international application) was mutated from Ser to Ala. When transfected and cultured in a host cell, the resulting vector pD12HZHC 1-0pcd produces humanized heavy chain D12HZHC 1-0 shown in SEQ ID NOS: 4 and 5.

ii. Construction of D12HZLC 1-0

A synthetic variable region humanized light chain was designed using a consensus human subgroup III kappa framework as defined by Kabat and the D12 murine light chain CDRs described previously. Three framework amino acids substitutions which might influence CDR presentation were made at AA residues 1, 49 and 60 [SEQ ID NOS: 9 and 10]. Four overlapping synthetic oligonucleotides were generated:

SBA1327:                                 [SEQ ID NO: 32]
    GACATAGTAC TGACTCAGTC TCCAGGCACC CTGTCTTTGT

CTCCAGGAGA AAGAGCCACC CTTTCCTGCA GGGCCAGCCA

AAGTATTAGC AACCACCTAC ACTGGTAT;

SBA1328:                                 [SEQ ID NO: 34]
    GCCACTGAAC CTGGAGGGGA TCCCAGAGAT GGACTGGGAA

GCATACTTGA TGAGAAGCCG CGGAGCCTGG CCAGGTTTTT

GTTGATACCA GTGTAGGTGG TTGCTAATAC TTTG;

SBA1329:                                 [SEQ ID NO: 34]
    TCTCTGGGAT CCCCTCCAGG TTCAGTGGCA GTGGATCAGG

GACAGATTTC ACTCTCACCA TCAGCCGTCT AGAGCCTGAA

GATTTTGCGG TTTATTACTG T; and

SBA1330:                                 [SEQ ID NO: 35]
    GGCGCCGCCA CAGTACGTTT TATTTCCACC TTGGTACCCT

GGCCGAACGT GAAAGGCCAG CTGTTACTCT GTTGACAGTA

ATAAACCGCA AAATCTTC.

When annealed and extended, these sequences code for amino acids representing the portion of the light chain variable region being altered including the first five amino acids of the human kappa constant region. SEQ ID NOS: 13 and 14, respectively, are the DNA and amino acid sequences of the intermediate of the synthetic light chain, i.e., representing the portion of the D12 light chain variable region being altered including the first five amino acids of the human kappa constant region. This synthetic gene was then amplified using PCR primers SBA1277: GACATAGTAC TGACTCAGTC TCCAGGC [SEQ ID NO: 36] and SBA1278: GGCGCCGCCA CAGTACG [SEQ ID NO: 37] and ligated into the pCR2000 vector described above and isolated after a ScaI, NarI restriction digest.

The DNA fragment coding for the Campath signal sequence [SEQ ID NOS: 18 and 19] including the first three amino acids of the variable region was made by PCRing the vector F9HZLCI-1 with certain primers. Vector F9HZLC1-1 is another variant of the pCDN vectors [Nambi el al, cited above] and pFHZLCL-1-pcn [International patent publication No. WO94/05690]. These pCN variant plasmid vectors contain, in general, a beta lactamase gene, an SV40 origin of replication, a cytomegalovirus promoter sequence, a selected humanized light chain, a polyA signal for bovine growth hormone, a betaglobin promoter, a neomycin resistance gene and another BGH sequence polyA signal in a pUC19 background. F9HZLC1-1 further contains the remainder of a human framework 4 and kappa constant region and a single amino acid mutation of the pFHZLCL-1-pcn vector in framework 2 (from Ser to Pro). The PCR primers used were SB8694: GGAGACGCCA TCGAAT-TCTG A [SEQ ID NO: 38] and SBA1224: AGACTGTGTC AGTACTATGT CGGAGTGGAC ACC [SEQ ID NO: 39] and F9HZLC1-1 was restriction digested with EcoRI and ScaI. These two fragments were ligated into the vector pFHZLCL-1-pcn, restriction digested with EcoRI and NarI. The resulting vector pD12HZLC 1-1-pcn, when cultured in a host cell produces humanized D12HZLC 1-0 [SEQ ID NOS: 9 and 10].

D. Expression of Humanized Antibody in Mammalian Cells

The heavy chain vector pD12HZHC 1-0pcd and light chain vector pD12HZLC 1-1-pcn described above were used to produce antibody HuD12 in COS cells and in CHO cells.

For initial characterization, the humanized HuD12 heavy and light chains were expressed in COS cells essentially as described in Current Protocols in Molecular Biology (edited by F. M. Ausubel et al. 1988, John Wiley & Sons, vol. 1, section 9.1). Briefly described, the COS cells were co transfected with 10 μg of each plasmid. On day 1 after the transfection, the culture growth medium was replaced with a serum-free medium which was changed on day 3. The serum-free medium was a proprietary formulation, but satisfactory results are obtained using DMEM supplemented with ITS™ Premix (insulin, transferrin, selenium mixture—Collaborative Research, Bedford, Mass.) and 1 mg/ml BSA. The mAb was isolated and prepared from the day 3+day 5 conditioned medium by standard protein A affinity chromatography methods (e.g., as described in Protocols in Molecular Biology) using, for example, Prosep A affinity resin (Bioprocessing Ltd., UK).

The humanized D12 was expressed as a γ1, kappa molecule in transiently transfected COS cells. The supernatants of this culture were found to bind to the α$_v$β$_3$ receptor in both ELISA and BIAcore assays described above.

To produce larger quantities of the HuD12 mAbs (100–200 mgs), the plasmids were introduced into a proprietary CHO cell system, the CHO-E1a cell line. This cell line supplies larger quantities of mAbs (approximately 10 mg of each) and enables testing of the activity profile of both chimeric and humanized antibodies. However, similar results will be obtained using dhfr⁻ CHO cells as previously described [P. Hensley et al., cited above]. Briefly, a total of 30 μg of linearized plasmid DNA (15 ug each of the heavy or light chain plasmids) is electroporated into 1×10$^7$ cells. The cells are initially selected in nucleoside-free medium in 96 well plates. After three to four weeks, media from growth positive wells is screened for human immunoglobulin using the ELISA assay of Example 3. The highest expressing colonies are expanded and selected in increasing concentrations of methotrexate for amplification of the transfected vectors. The antibody is purified from conditioned medium by standard procedures using protein A affinity chromatography (Protein A sepharose, Pharmacia) followed by size exclusion chromatography (Superdex 200, Pharmacia).

The concentration and the antigen binding activity of the eluted antibody are measured by the ELISA assays of Examples 3 and 4. The antibody containing fractions are pooled and further purified by size exclusion chromatography.

Two such humanized D12 antibodies have been generated, the IgG$_1$ antibody described above and an IgG$_4$ version (prepared analogously as described above, but using an IgG$_4$ constant region). The HZ-D12 (IgG$_1$) is produced in a stable CHO expression cell line. A 50 nM MTX line was generated that is acceptable for Phase I production (300 mg/L). Additional lines, i.e., 150 nM MTX line (400 mg/L) and 450 nM MTX line, are being evaluated. Murine and humanized D12 cross reacts with VSMC from baboon and inhibits SMC. Murine and humanized D12 inhibits human EC migration.

EXAMPLE 14

Construction of D12HZREI

A second construct has a light chain based on the REI consensus framework to provide an alternative light chain in the event of unstable expression in humanized D12 production cell lines. The primary variant introduces five murine framework residues predicted to make contact with different VK CDR residues.

Briefly described, a synthetic humanized kappa chain was designed based on a modified human REI kappa chain framework and the D12 CDRs described previously. SEQ ID NO: 15 is the amino acid sequence of the modified human REI kappa chain framework. Five donor (murine D12) framework residues were introduced, at positions identified in modeling experiments, which might influence CDR presentation. Four overlapping synthetic oligonucleotides were generated:

SBA 3166: [SEQ ID NO: 40]
5' gac atA GTA CTG ACT CAG TCT CCA AGC AGC CTG TCT

GCG TCT GTA GGA GAT AGA GTC ACC ATT ACC TGC AGG

GCC AGC CAA AGT ATT AGC 3';

SBA 3167: [SEQ ID NO: 41]
5' CCC GAG ATG GAC TGG GAA GCA TAC TTG ATG AGA AGC

CTA GGA GCC TTG CCA GGT TTT TGT TGA TAC CAG TGT

AGG TGG TTG CTA ATA CTT TGG CTG GCC CT 3';

SBA 3168: [SEQ ID NO:42]
5' GCT TCC GAG TCC ATC TCT GGG ATC CCC TCC AGG TTC

AgT GGC AGT GGA TCA GGG ACA GAT TTC ACT TTC ACC

ATC AGC AGT CTA GAG CCT GAA GAT ATT 3'; and

SBA 3169: [SEQ ID NO:43]
5' ttc cac ctt GGT ACC CTG GCC GAA CGT GAA AGG CCA

GGA ATT CGA CTG TTG ACA GTA ATA AGT CGC AAT ATC

TTC AGG CTG TAT ACT GCT 3'.

When these synthetic oligonucleotide sequences were annealed and extended, they code for amino acids representing the portion of the light chain variable region being altered, including the highly conserved KpnI site found in the Jk gene segment. SEQ ID NO: 16 illustrates the DNA sequence of the Jk gene segment and SEQ ID NO: 17 is the amino acid sequence of its gene product.

This synthetic gene was then amplified using two PCR primers SBA 3170: 5' gac atA GTA CTG ACT CAG TCT CCA AGC 3' [SEQ ID NO: 44]; and SBA 3171: 5' ttc cac ctt GGT ACC CTG GCC GAA CGT GAA AGG 3' [SEQ ID NO: 45], and ligated into the pCR2000 vector described above, and isolated after ScaI, KpnI digestion.

A DNA fragment corresponding to the CAMPATH signal sequence, illustrated in SEQ ID NOS: 18 and 19 was isolated following EcoRI, ScaI digestion of the light chain vector pD12HZLC 1-1 -pcn, described above. These two fragments were ligated together with the large fragment isolated from the same vector digested with EcoRI and KpnI which contains the k constant region. The resulting sequence was that of the synthetic light chain D12HZREI. SEQ ID NOS: 20 and 21 are the DNA sequence and the amino acid sequence, respectively, of the synthetic humanized kappa chain based on a modified human REI kappa chain framework, D12HZLCREI. Restriction enzyme endonuclease cleavage sites are located in the sequences as follows: ScaI (AGTACT; nucleotides 6–11), AvrII (CCTAGG; nucleotides 130–135); EcoRI (GAATTC; nucleotides 273–278) and KpnI (GGTACC; nucleotides 310–306).

EXAMPLE 15

In Vivo Rabbit Restenosis Assay

As described in Example 10, osteopontin, a ligand of the human α$_v$β$_3$ receptor, is upregulated following angioplasty and promotes VSMC migration via the integrin. Antibodies to human α$_v$β$_3$ receptor should prevent neointima formation in vivo.

The rabbit model functions as follows. On day 0, plasma samples are taken from normal 3 kg rabbits. The rabbits are then sedated, and the animals receive an injury (i.e., endothelial denudation of the iliac artery). Denudation of the endothelium is accomplished with three passes of a 3 fr embolectomy balloon catheter. Pilot studies indicates that the lesion incidence is 100% and 10–12 rabbits are needed in each group to detect a 35% reduction in neointimal area.

The murine D12 mAb was administered to the rabbits on days 1, 2 and 3. The dose was 9 mg/kg or 3 mg/kg delivered intravenously. Plasma samples are collected for mAb determinations on 0, 1, 2, and 21 days and morphometric analysis is performed on histologic sections prepared from each artery. Neointimal formation and vessel remodeling is then quantified 21 days following the injury. Increase in lumen area and total vessel area is indicative of remodeling after injury.

Figure 10A:
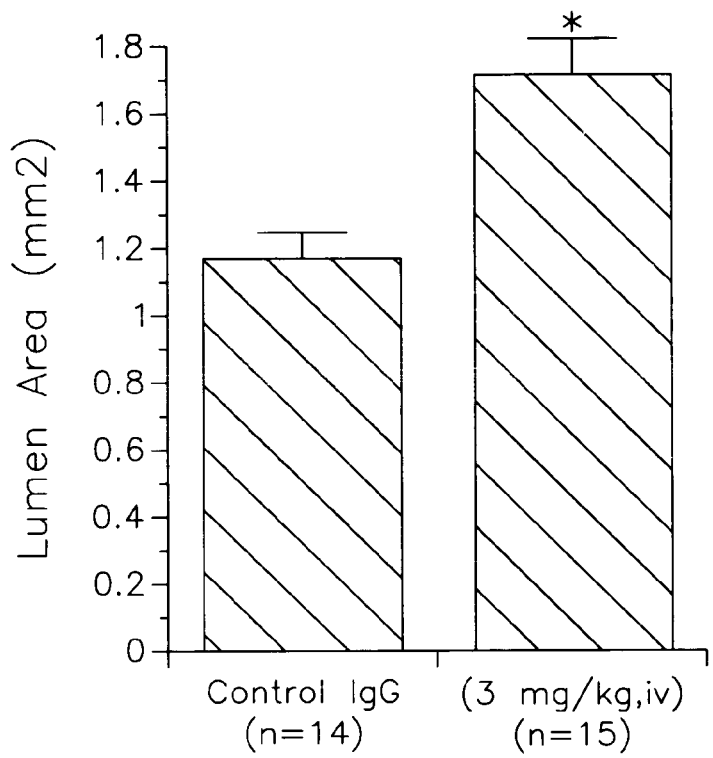
FIG. 10A is a bar graph illustrating the results of the rabbit restenosis assay of Example 15, measuring the effect on the lumen area of an injured vessel of treatment with a control or treatment with murine D12, delivered at a dosage of 3 mg/kg, i.v. N is the number of animals treated.
Figure 10B:
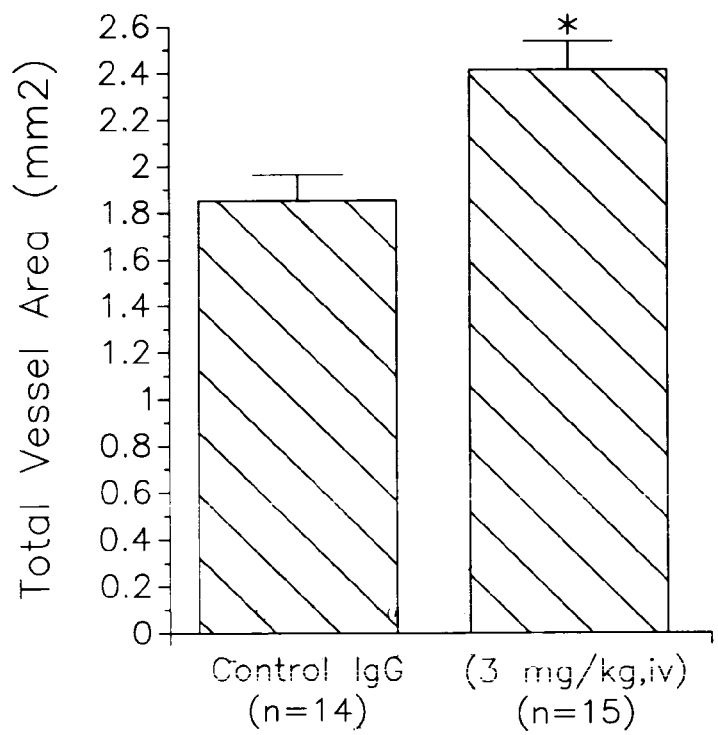
FIG. 10B is a bar graph illustrating the results of the rabbit restenosis assay measuring the effect on the total vessel area of the injured vessels treated as in FIG. 10A.
Figure 10C:
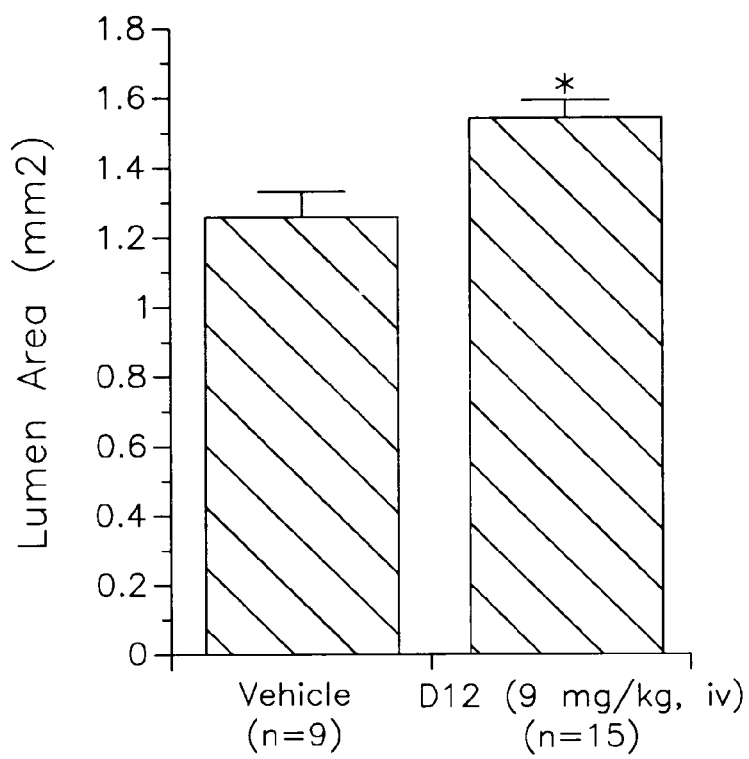
FIG. 10C is a bar graph similar to that of FIG. 10A, except that the murine D12 was delivered at a dosage of 9 mg/kg, i.v.
Figure 10D:
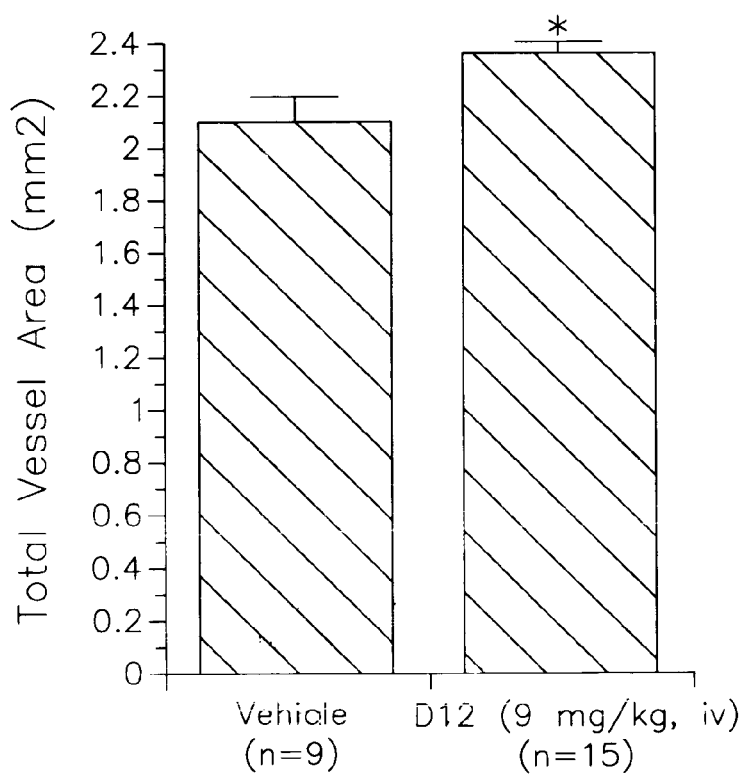
FIG. 10D is a bar graph similar to that of FIG. 10B, except that the murine D12 was delivered at a dosage of 9 mg/kg, i.v.

FIGS. 10A–10D illustrate the results of two separate studies. FIGS. 10A and 10C measure the lumen area treated by the control or the D12 mAb on Day 21 in two studies (2 doses). FIGS. 10B and 10D measure the total vessel area treated by the control of the D12 mAb in two studies (2 doses). This data indicates that murine D12 mAbs show efficacy in the rabbit model of restenosis, resulting in positive remodeling of the injured vessel (lumen enlargement).

EXAMPLE 16

SCID Model of Cancer/Angiogenesis

The severe combined immunodeficient mouse (SCID) model, in which human skin is grafted and not rejected [see, e.g., P. W. Soballe et al, 1996, *Cancer Res.* 56:757–764] can serve as a source of angiogenic neovascularization, and subsequently can accept human tumor. This model is utilized for efficacy testing of the D12 mAbs and HuD12 antibodies.

Briefly described, in this model human skin was grafted on the mouse. Human tumor cells are injected into the human skin graft and the growth of the tumor measured. The human skin graft supplies the human neovasculature required for tumor growth. The animals were treated with murine D12 or humanized D12 and the delay in the tumor growth compared to its untreated controls was observed.

Inhibition of tumor growth indicated that D12 mAbs (human anti-$\alpha_v\beta_3$ positive, murine anti-$\alpha_v\beta_3$ negative) play a role in the inhibition of $\alpha_v\beta_3$ dependent angiogenesis. Preliminary data indicated that tumor growth has been delayed in the animals treated with the D12 mAbs. These data support the hypothesis that treating "angiogenesis" will prevent tumor growth.

Table IV below indicates that by immunohistology the human skin has no positive anti-$\alpha_v\beta_3$ staining. However, when the tumor grows in the skin the neovasculature shows positive D12, indicating that $\alpha_v\beta_3$ is expressed in this tumor lesion.

TABLE IV

| Hu-SCID Tissue: | D12 mAb |
|---|---|
| human skin graft on SCID | − |
| human tumor growth in the skin graft | + |

The results of Examples 3 through 16 establish that the D12 and HuD12 antibodies have potent anti-receptor activity in vitro and show prophylactic and therapeutic efficacy in vivo in animal models.

It will be clear that the invention may be practiced otherwise than as particularly described in the foregoing description and examples. All published documents referred to herein are incorporated by reference. Numerous modifications and variations of the present invention are possible in light of the above teachings and, therefore, are within the scope of the appended claims.

What is claimed is:

1. An altered antibody specifically reactive with the human $\alpha_v\beta_3$ protein receptor and capable of neutralizing said receptor comprising a heavy chain comprising the complementarity determining region sequences corresponding to amino acids 31–35, amino acids 50–66, and amino acids 99–106 of SEQ ID NO:5.

2. The antibody according to claim 1 having a light chain comprising the complementarity determining region sequences corresponding to amino acids 24–34, amino acids 50–66, and amino acids 89–97 of SEQ ID NO:10.

3. The antibody according to claim 1 which comprises the light chain amino acid sequence of SEQ ID NO: 10 and the heavy chain amino acid sequence of SEQ ID NO: 5.

4. The antibody according to claim 1 which comprises the light chain amino acid sequence of SEQ ID NO: 15 and the heavy chain amino acid sequence of SEQ ID NO: 5.

5. The antibody according to claim 1 which comprises the heavy chain amino acid sequence of SEQ ID NO: 5 and a light chain of a human antibody.

6. An isolated murine monoclonal antibody and antigen binding fragments thereof, specifically reactive with the human GtvB3 receptor and capable of neutralizing said receptor, having a heavy chain comprising the complementarity determining region sequences corresponding to amino acids 31–35, amino acids 50–66, and amino acids 99–106 of SEQ ID NO: 2.

7. The antibody according to claim 6 having a light chain comprising the complementarity determining region sequences corresponding to amino acid residues 24–34, amino acid residues 50–56, and amino acid residues 89–97 of SEQ ID NO: 7.

8. The monoclonal antibody according to claim 6 which comprises the light chain amino acid sequence of SEQ ID NO: 7 and the heavy chain amino acid sequence of SEQ ID NO: 2.

9. A pharmaceutical composition comprising at least one dose of an immunotherapeutically effective amount of the antibody of claim 1 in a pharmaceutically acceptable carrier.

10. A method of detecting a disorder characterized by overexpression of the human $\alpha v \beta 3$ receptor comprising contacting a source suspected of containing overexpressed human $\alpha v \beta B3$ receptor with a diagnostically effective amount of the antibody of claim 1 and measuring the binding of the antibody to the source.

* * * * *

SEQUENCE LISTING

<160> NUMBER OF SEQ ID NOS: 45

<210> SEQ ID NO 1
<211> LENGTH: 351
<212> TYPE: DNA
<213> ORGANISM: Mus musculus
<220> FEATURE:
<221> NAME/KEY: CDS
<222> LOCATION: (1)...(351)

<400> SEQUENCE: 1

```
gag atc cag ctg caa caa tct gga cct gag gtg gtg aag cct ggg gcc        48
Glu Ile Gln Leu Gln Gln Ser Gly Pro Glu Val Val Lys Pro Gly Ala
 1               5                  10                  15 tca gtg aag gta tcc tgc aag gct tct ggt tat gca ttc act agc tac        96
Ser Val Lys Val Ser Cys Lys Ala Ser Gly Tyr Ala Phe Thr Ser Tyr
             20                  25                  30 aac atg tac tgg gtg aag cag agc cat gga aag agc ctt gag tgg att       144
Asn Met Tyr Trp Val Lys Gln Ser His Gly Lys Ser Leu Glu Trp Ile
         35                  40                  45 gga tat att gat cct tac aat ggt gat act ttc tac aac cag aaa ttc       192
Gly Tyr Ile Asp Pro Tyr Asn Gly Asp Thr Phe Tyr Asn Gln Lys Phe
     50                  55                  60 aag ggc aag gcc aca ttg act gtt gac aag tcc tcc agc aca gcc tac       240
Lys Gly Lys Ala Thr Leu Thr Val Asp Lys Ser Ser Ser Thr Ala Tyr
 65                  70                  75                  80
```

```
atg cat ctc aac agc ctg aca tct gag gac tct gca gtc ttt tac tgt        288
Met His Leu Asn Ser Leu Thr Ser Glu Asp Ser Ala Val Phe Tyr Cys
            85                  90                  95 gca aga cag aac tac ggt agt ttt gct tac tgg ggc caa ggg act ctg        336
Ala Arg Gln Asn Tyr Gly Ser Phe Ala Tyr Trp Gly Gln Gly Thr Leu
            100                 105                 110 gtc act gtc tct gcg                                                    351
Val Thr Val Ser Ala
            115
```

<210> SEQ ID NO 2
<211> LENGTH: 117
<212> TYPE: PRT
<213> ORGANISM: Mus musculus

<400> SEQUENCE: 2

```
Glu Ile Gln Leu Gln Gln Ser Gly Pro Glu Val Val Lys Pro Gly Ala
 1               5                  10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Thr Phe Tyr Asn Gln Lys Phe
    50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Phe Tyr Cys
            85                  90                  95

Ala Arg Gln Asn Tyr Gly Ser Phe Ala Tyr Trp Gly Gln Gly Thr Leu
            100                 105                 110

Val Thr Val Ser Ala
            115
```

<210> SEQ ID NO 3
<211> LENGTH: 115
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Trp Ile Asn Pro Gly Gly Asp Thr Asn Tyr Ala Gln Lys Phe Gln Gly
    50                  55                  60

Arg Val Thr Ile Thr Ala Asp Thr Ser Thr Ser Thr Ala Tyr Met Glu
65                  70                  75                  80

Leu Ser Ser Leu Arg Ser Glu Asp Thr Ala Val Tyr Tyr Cys Ala Arg
            85                  90                  95

Pro Gly Tyr Gly Tyr Tyr Gly Tyr Trp Gly Gln Gly Thr Leu Val Thr
            100                 105                 110

Val Ser Ser
        115
```

<210> SEQ ID NO 4

```
<211> LENGTH: 351
<212> TYPE: DNA
<213> ORGANISM: Homo sapiens
<220> FEATURE:
<221> NAME/KEY: CDS
<222> LOCATION: (1)...(351)

<400> SEQUENCE: 4 cag gtg caa cta gtg cag tct gga gct gag gtg aag aag cct ggg gcc         48
Gln Val Gln Leu Val Gln Ser Gly Ala Glu Val Lys Lys Pro Gly Ala
 1               5                  10                  15 tca gtg aag gta tcc tgc aaa gct tct ggt tat gca ttc act agc tac         96
Ser Val Lys Val Ser Cys Lys Ala Ser Gly Tyr Ala Phe Thr Ser Tyr
             20                  25                  30 aac atg tac tgg gtg cgg cag gcc cct gga cag ggt cta gag tgg att        144
Asn Met Tyr Trp Val Arg Gln Ala Pro Gly Gln Gly Leu Glu Trp Ile
         35                  40                  45 gga tat att gat cct tac aat ggt gat act ttc tac aac cag aaa ttc        192
Gly Tyr Ile Asp Pro Tyr Asn Gly Asp Thr Phe Tyr Asn Gln Lys Phe
     50                  55                  60 aag ggc aag gcc aca ttg act gtc gac aag tcc acc agc aca gcc tac        240
Lys Gly Lys Ala Thr Leu Thr Val Asp Lys Ser Thr Ser Thr Ala Tyr
 65                  70                  75                  80 atg gaa ctc agc agc ctg aga tct gag gac act gca gtc tat tac tgt        288
Met Glu Leu Ser Ser Leu Arg Ser Glu Asp Thr Ala Val Tyr Tyr Cys
                 85                  90                  95 gca aga cag aac tac ggt agt ttt gct tac tgg ggc caa ggt acc ctg        336
Ala Arg Gln Asn Tyr Gly Ser Phe Ala Tyr Trp Gly Gln Gly Thr Leu
            100                 105                 110 gtc act gtc tct tcg                                                    351
Val Thr Val Ser Ser
            115

<210> SEQ ID NO 5
<211> LENGTH: 117
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Ser Tyr
             20                  25                  30

Asn Met Tyr Trp Val Arg Gln Ala Pro Gly Gln Gly Leu Glu Trp Ile
         35                  40                  45

Gly Tyr Ile Asp Pro Tyr Asn Gly Asp Thr Phe Tyr Asn Gln Lys Phe
     50                  55                  60

Lys Gly Lys Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gln Asn Tyr Gly Ser Phe Ala Tyr Trp Gly Gln Gly Thr Leu
            100                 105                 110

Val Thr Val Ser Ser
            115

<210> SEQ ID NO 6
<211> LENGTH: 324
<212> TYPE: DNA
<213> ORGANISM: Mus musculus
<220> FEATURE:
```

```
<221> NAME/KEY: CDS
<222> LOCATION: (1)...(324)

<400> SEQUENCE: 6 gac att gtg ctg act cag tct cca gcc acc ctg tct gtg act cca gga      48
Asp Ile Val Leu Thr Gln Ser Pro Ala Thr Leu Ser Val Thr Pro Gly
 1               5                  10                  15 gat agc gtc agt ctt tcc tgc agg gcc agc caa agt att agc aac cac      96
Asp Ser Val Ser Leu Ser Cys Arg Ala Ser Gln Ser Ile Ser Asn His
             20                  25                  30 cta cac tgg tat caa caa aga tca cat gag tct cca agg ctt ctc atc     144
Leu His Trp Tyr Gln Gln Arg Ser His Glu Ser Pro Arg Leu Leu Ile
         35                  40                  45 aag tat gct tcc cag tcc atc tct ggg atc ccc tcc agg ttc aga ggc     192
Lys Tyr Ala Ser Gln Ser Ile Ser Gly Ile Pro Ser Arg Phe Arg Gly
     50                  55                  60 agt gga tca ggg aca gat ttc act ctc aat atc aac att ttg gag act     240
Ser Gly Ser Gly Thr Asp Phe Thr Leu Asn Ile Asn Ile Leu Glu Thr
 65                  70                  75                  80 gag gat ttt gga atg tat ttc tgt caa cag agt aac agc tgg cct ttc     288
Glu Asp Phe Gly Met Tyr Phe Cys Gln Gln Ser Asn Ser Trp Pro Phe
                 85                  90                  95 acg ttc ggc tcg ggg aca aac ttg gaa ata aaa cgg                     324
Thr Phe Gly Ser Gly Thr Asn Leu Glu Ile Lys Arg
            100                 105

<210> SEQ ID NO 7
<211> LENGTH: 108
<212> TYPE: PRT
<213> ORGANISM: Mus musculus

<400> SEQUENCE: 7

Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Ser Asn His
             20                  25                  30

Leu His Trp Tyr Gln Gln Arg Ser His Glu Ser Pro Arg Leu Leu Ile
         35                  40                  45

Lys Tyr Ala Ser Gln Ser Ile Ser Gly Ile Pro Ser Arg Phe Arg Gly
     50                  55                  60

Ser Gly Ser Gly Thr Asp Phe Thr Leu Asn Ile Asn Ile Leu Glu Thr
 65                  70                  75                  80

Glu Asp Phe Gly Met Tyr Phe Cys Gln Gln Ser Asn Ser Trp Pro Phe
                 85                  90                  95

Thr Phe Gly Ser Gly Thr Asn Leu Glu Ile Lys Arg
            100                 105

<210> SEQ ID NO 8
<211> LENGTH: 109
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45
```

```
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Leu Thr Phe Gly Gln Gly Thr Lys Val Glu Ile Lys
            100                 105
```

<210> SEQ ID NO 9
<211> LENGTH: 321
<212> TYPE: DNA
<213> ORGANISM: Artificial Sequence
<220> FEATURE:
<221> NAME/KEY: CDS
<222> LOCATION: (1)...(321)
<223> OTHER INFORMATION: Synthetic light chain nucleotide and amino acid
      sequences of the humanized light chain
      D12HZLC-1-0.

<400> SEQUENCE: 9

```
gac ata gta ctg act cag tct cca ggc acc ctg tct ttg tct cca gga     48
Asp Ile Val Leu Thr Gln Ser Pro Gly Thr Leu Ser Leu Ser Pro Gly
 1               5                  10                  15 gaa aga gcc acc ctt tcc tgc agg gcc agc caa agt att agc aac cac     96
Glu Arg Ala Thr Leu Ser Cys Arg Ala Ser Gln Ser Ile Ser Asn His
                20                  25                  30 cta cac tgg tat caa caa aaa cct ggc cag gct ccg cgg ctt ctc atc    144
Leu His Trp Tyr Gln Gln Lys Pro Gly Gln Ala Pro Arg Leu Leu Ile
            35                  40                  45 aag tat gct tcc cag tcc atc tct ggg atc ccc tcc agg ttc agt ggc    192
Lys Tyr Ala Ser Gln Ser Ile Ser Gly Ile Pro Ser Arg Phe Ser Gly
 50                  55                  60 agt gga tca ggg aca gat ttc act ctc acc atc agc cgt cta gag cct    240
Ser Gly Ser Gly Thr Asp Phe Thr Leu Thr Ile Ser Arg Leu Glu Pro
 65                  70                  75                  80 gaa gat ttt gcg gtt tat tac tgt caa cag agt aac agc tgg cct ttc    288
Glu Asp Phe Ala Val Tyr Tyr Cys Gln Gln Ser Asn Ser Trp Pro Phe
                 85                  90                  95 acg ttc ggc cag ggt acc aag gtg gaa ata aaa                        321
Thr Phe Gly Gln Gly Thr Lys Val Glu Ile Lys
            100                 105
```

<210> SEQ ID NO 10
<211> LENGTH: 107
<212> TYPE: PRT
<213> ORGANISM: Artificial Sequence
<220> FEATURE:
<223> OTHER INFORMATION: Synthetic light chain nucleotide and amino acid
      sequences of the humanized light chain
      D12HZLC-1-0.

<400> SEQUENCE: 10

```
Asp Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Ser Asn His
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Thr Ile Ser Arg Leu Glu Pro
```

```
                    65                  70                  75                  80
Glu Asp Phe Ala Val Tyr Tyr Cys Gln Gln Ser Asn Ser Trp Pro Phe
                    85                  90                  95

Thr Phe Gly Gln Gly Thr Lys Val Glu Ile Lys
                100                 105
```

<210> SEQ ID NO 11
<211> LENGTH: 333
<212> TYPE: DNA
<213> ORGANISM: Mus musculus
<220> FEATURE:
<221> NAME/KEY: CDS
<222> LOCATION: (3)...(332)

<400> SEQUENCE: 11

```
tg caa cta gtg cag tct gga gct gag gtg aag aag cct ggg gcc tca        47
   Gln Leu Val Gln Ser Gly Ala Glu Val Lys Lys Pro Gly Ala Ser
     1               5                  10                  15 gtg aag gta tcc tgc aaa gct tct ggt tat gca ttc act agc tac aac       95
Val Lys Val Ser Cys Lys Ala Ser Gly Tyr Ala Phe Thr Ser Tyr Asn
                 20                  25                  30 atg tac tgg gtg cgg cag gcc cct gga cag ggt cta gag tgg att gga      143
Met Tyr Trp Val Arg Gln Ala Pro Gly Gln Gly Leu Glu Trp Ile Gly
             35                  40                  45 tat att gat cct tac aat ggt gat act ttc tac aac cag aaa ttc aag      191
Tyr Ile Asp Pro Tyr Asn Gly Asp Thr Phe Tyr Asn Gln Lys Phe Lys
         50                  55                  60 ggc aag gcc aca ttg act gtc gac aag tcc acc agc aca gcc tac atg      239
Gly Lys Ala Thr Leu Thr Val Asp Lys Ser Thr Ser Thr Ala Tyr Met
 65                  70                  75 gaa ctc agc agc ctg aga tct gag gac act gca gtc tat tac tgt gca      287
Glu Leu Ser Ser Leu Arg Ser Glu Asp Thr Ala Val Tyr Tyr Cys Ala
 80                  85                  90                  95 aga cag aac tac ggt agt ttt gct tac tgg ggc caa ggt acc ctg          332
Arg Gln Asn Tyr Gly Ser Phe Ala Tyr Trp Gly Gln Gly Thr Leu
                100                 105                 110 g                                                                    333
```

<210> SEQ ID NO 12
<211> LENGTH: 110
<212> TYPE: PRT
<213> ORGANISM: Mus musculus

<400> SEQUENCE: 12

```
Gln Leu Val Gln Ser Gly Ala Glu Val Lys Lys Pro Gly Ala Ser Val
 1               5                  10                  15

Lys Val Ser Cys Lys Ala Ser Gly Tyr Ala Phe Thr Ser Tyr Asn Met
             20                  25                  30

Tyr Trp Val Arg Gln Ala Pro Gly Gln Gly Leu Glu Trp Ile Gly Tyr
         35                  40                  45

Ile Asp Pro Tyr Asn Gly Asp Thr Phe Tyr Asn Gln Lys Phe Lys Gly
     50                  55                  60

Lys Ala Thr Leu Thr Val Asp Lys Ser Thr Ser Thr Ala Tyr Met Glu
 65                  70                  75                  80

Leu Ser Ser Leu Arg Ser Glu Asp Thr Ala Val Tyr Tyr Cys Ala Arg
                 85                  90                  95

Gln Asn Tyr Gly Ser Phe Ala Tyr Trp Gly Gln Gly Thr Leu
                100                 105                 110
```

```
<210> SEQ ID NO 13
<211> LENGTH: 338
<212> TYPE: DNA
<213> ORGANISM: Mus Musculus
<220> FEATURE:
<221> NAME/KEY: CDS
<222> LOCATION: (1)...(336)

<400> SEQUENCE: 13 gac ata gta ctg act cag tct cca ggc acc ctg tct ttg tct cca gga        48
Asp Ile Val Leu Thr Gln Ser Pro Gly Thr Leu Ser Leu Ser Pro Gly
  1               5                  10                  15 gaa aga gcc acc ctt tcc tgc agg gcc agc caa agt att agc aac cac        96
Glu Arg Ala Thr Leu Ser Cys Arg Ala Ser Gln Ser Ile Ser Asn His
             20                  25                  30 cta cac tgg tat caa caa aaa cct ggc cag gct ccg cgg ctt ctc atc       144
Leu His Trp Tyr Gln Gln Lys Pro Gly Gln Ala Pro Arg Leu Leu Ile
         35                  40                  45 aag tat gct tcc cag tcc atc tct ggg atc ccc tcc agg ttc agt ggc       192
Lys Tyr Ala Ser Gln Ser Ile Ser Gly Ile Pro Ser Arg Phe Ser Gly
     50                  55                  60 agt gga tca ggg aca gat ttc act ctc acc atc agc cgt cta gag cct       240
Ser Gly Ser Gly Thr Asp Phe Thr Leu Thr Ile Ser Arg Leu Glu Pro
 65                  70                  75                  80 gaa gat ttt gcg gtt tat tac tgt caa cag agt aac agc tgg cct ttc       288
Glu Asp Phe Ala Val Tyr Tyr Cys Gln Gln Ser Asn Ser Trp Pro Phe
                 85                  90                  95 acg ttc ggc cag ggt acc aag gtg gaa ata aaa cgt act gtg gcg gcg       336
Thr Phe Gly Gln Gly Thr Lys Val Glu Ile Lys Arg Thr Val Ala Ala
                100                 105                 110 cc                                                                    338

<210> SEQ ID NO 14
<211> LENGTH: 112
<212> TYPE: PRT
<213> ORGANISM: Mus Musculus

<400> SEQUENCE: 14

Asp Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Ile Ser Asn His
             20                  25                  30

Leu His Trp Tyr Gln Gln Lys Pro Gly Gln Ala Pro Arg Leu Leu Ile
         35                  40                  45

Lys Tyr Ala Ser Gln Ser Ile Ser Gly Ile Pro Ser Arg Phe Ser Gly
     50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Ser Asn Ser Trp Pro Phe
                 85                  90                  95

Thr Phe Gly Gln Gly Thr Lys Val Glu Ile Lys Arg Thr Val Ala Ala
                100                 105                 110

<210> SEQ ID NO 15
<211> LENGTH: 107
<212> TYPE: PRT
<213> ORGANISM: Artificial Sequence
<220> FEATURE:
<223> OTHER INFORMATION: Represents an amino acid sequence of the
      modified human REI kappa chain framework

<400> SEQUENCE: 15
```

```
Asp Ile Gln Met Thr Gln Ser Pro Ser Leu Ser Ala Ser Val Gly
 1               5                  10                 15

Asp Arg Val Thr Ile Thr Cys Gln Ala Ser Gln Asp Ile Ile Lys Tyr
             20                  25                  30

Leu Asn Trp Tyr Gln Gln Lys Pro Gly Lys Ala Pro Lys Leu Leu Ile
         35                  40                  45

Tyr Glu Ala Ser Asn Leu Gln Ala Gly Val Pro Ser Arg Phe Ser Gly
 50                  55                  60

Ser Gly Ser Gly Thr Asp Phe Thr Phe Thr Ile Ser Ser Leu Gln Pro
65               70                  75                  80

Glu Asp Ile Ala Thr Tyr Tyr Cys Gln Gln Tyr Gln Ser Leu Pro Tyr
                 85                  90                  95

Thr Phe Gly Gln Gly Thr Lys Val Glu Ile Lys
            100                 105

<210> SEQ ID NO 16
<211> LENGTH: 315
<212> TYPE: DNA
<213> ORGANISM: Artificial Sequence
<220> FEATURE:
<221> NAME/KEY: CDS
<222> LOCATION: (1)...(315)
<223> OTHER INFORMATION: Wherein the sequences represent the DNA and
      amino acid sequences of the Jk gene and its gene product.

<400> SEQUENCE: 16 gac ata gta ctg act cag tct cca agc agc ctg tct gcg tct gta gga        48
Asp Ile Val Leu Thr Gln Ser Pro Ser Ser Leu Ser Ala Ser Val Gly
 1               5                  10                  15 gat aga gtc acc att acc tgc agg gcc agc caa agt att agc aac cac        96
Asp Arg Val Thr Ile Thr Cys Arg Ala Ser Gln Ser Ile Ser Asn His
             20                  25                  30 cta cac tgg tat caa caa aaa cct ggc aag gct cct agg ctt ctc atc       144
Leu His Trp Tyr Gln Gln Lys Pro Gly Lys Ala Pro Arg Leu Leu Ile
         35                  40                  45 aag tat gct tcc cag tcc atc tct ggg atc ccc tcc agg ttc agt ggc       192
Lys Tyr Ala Ser Gln Ser Ile Ser Gly Ile Pro Ser Arg Phe Ser Gly
 50                  55                  60 agt gga tca ggg aca gat ttc act ttc acc atc agc agt cta cag cct       240
Ser Gly Ser Gly Thr Asp Phe Thr Phe Thr Ile Ser Ser Leu Gln Pro
65               70                  75                  80 gaa gat att gcg act tat tac tgt caa cag tcg aat tcc tgg cct ttc       288
Glu Asp Ile Ala Thr Tyr Tyr Cys Gln Gln Ser Asn Ser Trp Pro Phe
                 85                  90                  95 acg ttc ggc cag ggt acc aag gtg gaa                                   315
Thr Phe Gly Gln Gly Thr Lys Val Glu
            100                 105

<210> SEQ ID NO 17
<211> LENGTH: 105
<212> TYPE: PRT
<213> ORGANISM: Artificial Sequence
<220> FEATURE:
<223> OTHER INFORMATION: Wherein the sequences represent the DNA and
      amino acid sequences of the Jk gene and its gene product.

<400> SEQUENCE: 17

Asp Ile Val Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn His
             20                  25                  30
```

```
Leu His Trp Tyr Gln Gln Lys Pro Gly Lys Ala Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Asn Ser Trp Pro Phe
                85                  90                  95

Thr Phe Gly Gln Gly Thr Lys Val Glu
                100                 105

<210> SEQ ID NO 18
<211> LENGTH: 94
<212> TYPE: DNA
<213> ORGANISM: Artificial Sequence
<220> FEATURE:
<221> NAME/KEY: CDS
<222> LOCATION: (27)...(92)
<223> OTHER INFORMATION: Wherein the sequences represent the DNA and
      amino acid sequences of the CAMPATH signal sequence.

<400> SEQUENCE: 18
gaattctgag cacacaggac ctcacc atg gga tgg agc tgt atc atc ctc ttc      53
                             Met Gly Trp Ser Cys Ile Ile Leu Phe
                              1               5 ttg gta gca aca gct aca ggt gtc cac tcc gac ata gta ct               94
Leu Val Ala Thr Ala Thr Gly Val His Ser Asp Ile Val
 10                  15                  20

<210> SEQ ID NO 19
<211> LENGTH: 22
<212> TYPE: PRT
<213> ORGANISM: Artificial Sequence
<220> FEATURE:
<223> OTHER INFORMATION: Wherein the sequences represent the DNA and
      amino acid sequences of the CAMPATH signal sequence.

<400> SEQUENCE: 19

Met Gly Trp Ser Cys Ile Ile Leu Phe Leu Val Ala Thr Ala Thr Gly
 1               5                  10                  15

Val His Ser Asp Ile Val
            20

<210> SEQ ID NO 20
<211> LENGTH: 315
<212> TYPE: DNA
<213> ORGANISM: Artificial Sequence
<220> FEATURE:
<221> NAME/KEY: CDS
<222> LOCATION: (1)...(315)
<223> OTHER INFORMATION: Represents an amino acid sequence of the
      synthetic kappa chain based on a modified human REI kappa
      chain framework

<400> SEQUENCE: 20 gac ata gta ctg act cag tct cca agc agc ctg tct gcg tct gta gga      48
Asp Ile Val Leu Thr Gln Ser Pro Ser Ser Leu Ser Ala Ser Val Gly
 1               5                  10                  15 gat aga gtc acc att acc tgc agg gcc agc caa agt att agc aac cac      96
Asp Arg Val Thr Ile Thr Cys Arg Ala Ser Gln Ser Ile Ser Asn His
                20                  25                  30 cta cac tgg tat caa caa aaa cct ggc aag gct cct agg ctt ctc atc     144
Leu His Trp Tyr Gln Gln Lys Pro Gly Lys Ala Pro Arg Leu Leu Ile
            35                  40                  45
```

```
aag tat gct tcc cag tcc atc tct ggg atc ccc tcc agg ttc agt ggc      192
Lys Tyr Ala Ser Gln Ser Ile Ser Gly Ile Pro Ser Arg Phe Ser Gly
 50                  55                  60 agt gga tca ggg aca gat ttc act ttc acc atc agc agt cta cag cct      240
Ser Gly Ser Gly Thr Asp Phe Thr Phe Thr Ile Ser Ser Leu Gln Pro
 65                  70                  75                  80 gaa gat att gcg act tat tac tgt caa cag tcg aat tcc tgg cct ttc      288
Glu Asp Ile Ala Thr Tyr Tyr Cys Gln Gln Ser Asn Ser Trp Pro Phe
                 85                  90                  95 acg ttc ggc cag ggt acc aag gtg gaa                                  315
Thr Phe Gly Gln Gly Thr Lys Val Glu
            100                 105
```

<210> SEQ ID NO 21
<211> LENGTH: 105
<212> TYPE: PRT
<213> ORGANISM: Artificial Sequence
<220> FEATURE:
<223> OTHER INFORMATION: Represents an amino acid sequence of the
      synthetic kappa chain based on a modified human REI kappa
      chain framework

<400> SEQUENCE: 21

```
Asp Ile Val Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn His
             20                  25                  30

Leu His Trp Tyr Gln Gln Lys Pro Gly Lys Ala Pro Arg Leu Leu Ile
         35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Asn Ser Trp Pro Phe
                 85                  90                  95

Thr Phe Gly Gln Gly Thr Lys Val Glu
            100                 105
```

<210> SEQ ID NO 22
<211> LENGTH: 23
<212> TYPE: DNA
<213> ORGANISM: Mus musculus

<400> SEQUENCE: 22

```
tcttgtccac cttggtgctg ctg                                             23
```

<210> SEQ ID NO 23
<211> LENGTH: 17
<212> TYPE: PRT
<213> ORGANISM: Mus musculus

<400> SEQUENCE: 23

```
Ser Trp Arg Gly Thr Tyr Cys Ala Arg Cys Thr Asx Cys Ala Arg Cys
 1               5                  10                  15

Ala
```

<210> SEQ ID NO 24
<211> LENGTH: 21
<212> TYPE: DNA
<213> ORGANISM: Mus musculus

```
<400> SEQUENCE: 24
gcacctccag atgttaactg c                                            21

<210> SEQ ID NO 25
<211> LENGTH: 28
<212> TYPE: DNA
<213> ORGANISM: Mus musculus

<400> SEQUENCE: 25
gacattgtgc tgactcagtc tccagcca                                     28

<210> SEQ ID NO 26
<211> LENGTH: 100
<212> TYPE: DNA
<213> ORGANISM: Mus musculus

<400> SEQUENCE: 26
tgcaactagt gcagtctgga gctgaggtga agaagcctgg ggcctcagtg aaggtatcct  60
gcaaagcttc tggttatgca ttcactagct acaacatgta                       100

<210> SEQ ID NO 27
<211> LENGTH: 114
<212> TYPE: DNA
<213> ORGANISM: Mus musculus

<400> SEQUENCE: 27
ttgcccttga atttctggtt gtagaaagta tcaccattgt aaggatcaat atatccaatc  60
cactctagac cctgtccagg ggcctgccgc acccagtaca tgttgtagct agtg       114

<210> SEQ ID NO 28
<211> LENGTH: 102
<212> TYPE: DNA
<213> ORGANISM: Mus musculus

<400> SEQUENCE: 28
ctacaaccag aaattcaagg gcaaggccac attgactgtc gacaagtcca ccagcacagc  60
ctacatggaa ctcagcagcc tgagatctga ggacactgca gt                   102

<210> SEQ ID NO 29
<211> LENGTH: 89
<212> TYPE: DNA
<213> ORGANISM: Mus musculus

<400> SEQUENCE: 29
ccagggtacc ttggccccag taagcaaaac taccgtagtt ctgtcttgca cagtaataga  60
ctgcagtgtc ctcagatctc aggctgctg                                   89

<210> SEQ ID NO 30
<211> LENGTH: 28
<212> TYPE: DNA
<213> ORGANISM: Artificial Sequence
<220> FEATURE:
<223> OTHER INFORMATION: PCR primer SBA883 used to amplify the synthetic
      gene.

<400> SEQUENCE: 30
tgcaactagt gcagtctgga gctgaggt                                     28

<210> SEQ ID NO 31
<211> LENGTH: 20
<212> TYPE: DNA
```

<213> ORGANISM: Artificial Sequence
<220> FEATURE:
<223> OTHER INFORMATION: PCR primer SBA884 used to amplify the synthetic gene.

<400> SEQUENCE: 31
ccagggtacc ttggccccag                                          20

<210> SEQ ID NO 32
<211> LENGTH: 108
<212> TYPE: DNA
<213> ORGANISM: Artificial Sequence
<220> FEATURE:
<223> OTHER INFORMATION: Overlapping synthetic oligonucleotides which, when annealed and extended, represent the portion of the light chain variable region being altered.

<400> SEQUENCE: 32
gacatagtac tgactcagtc tccaggcacc ctgtctttgt ctccaggaga aagagccacc    60
ctttcctgca gggccagcca agtattagc aaccacctac actggtat               108

<210> SEQ ID NO 33
<211> LENGTH: 114
<212> TYPE: DNA
<213> ORGANISM: Artificial Sequence
<220> FEATURE:
<223> OTHER INFORMATION: Overlapping synthetic oligonucleotides which, when annealed and extended, represent the portion of the light chain variable region being altered.

<400> SEQUENCE: 33
gccactgaac ctggagggga tcccagagat ggactgggaa gcatacttga tgagaagccg    60
cggagcctgg ccaggttttt gttgatacca gtgtaggtgg ttgctaatac tttg        114

<210> SEQ ID NO 34
<211> LENGTH: 101
<212> TYPE: DNA
<213> ORGANISM: Artificial Sequence
<220> FEATURE:
<223> OTHER INFORMATION: Overlapping synthetic oligonucleotides which, when annealed and extended, represent the portion of the light chain variable region being altered.

<400> SEQUENCE: 34
tctctgggat cccctccagg ttcagtggca gtggatcagg gacagatttc actctcacca    60
tcagccgtct agagcctgaa gattttgcgg tttattactg t                      101

<210> SEQ ID NO 35
<211> LENGTH: 98
<212> TYPE: DNA
<213> ORGANISM: Artificial Sequence
<220> FEATURE:
<223> OTHER INFORMATION: Overlapping synthetic oligonucleotides which, when annealed and extended, represent the portion of the light chain variable region being altered.

<400> SEQUENCE: 35
ggcgccgcca cagtacgttt tatttccacc ttggtaccct ggccgaacgt gaaaggccag    60
ctgttactct gttgacagta ataaaccgca aaatcttc                         98

<210> SEQ ID NO 36
<211> LENGTH: 27
<212> TYPE: DNA
<213> ORGANISM: Artificial Sequence
<220> FEATURE:

<223> OTHER INFORMATION: PCR Primer SBA1277 used to amplify the
      synthetic gene represented by SEQ IDS: 32, 33, 34, and 35.

<400> SEQUENCE: 36
gacatagtac tgactcagtc tccaggc                                         27

<210> SEQ ID NO 37
<211> LENGTH: 17
<212> TYPE: DNA
<213> ORGANISM: Artificial Sequence
<220> FEATURE:
<223> OTHER INFORMATION: PCR Primer SBA1277 used to amplify the
      synthetic gene represented by SEQ IDS: 32, 33, 34, and 35.

<400> SEQUENCE: 37
ggcgccgcca cagtacg                                                    17

<210> SEQ ID NO 38
<211> LENGTH: 21
<212> TYPE: DNA
<213> ORGANISM: Artificial Sequence
<220> FEATURE:
<223> OTHER INFORMATION: PCR Primer SB8694 which, in conjunction with
      the vector F9HZLC1-1, generates the DNA fragment coding for the
      Campath signal sequence.

<400> SEQUENCE: 38
ggagacgcca tcgaattctg a                                               21

<210> SEQ ID NO 39
<211> LENGTH: 33
<212> TYPE: DNA
<213> ORGANISM: Artificial Sequence
<220> FEATURE:
<223> OTHER INFORMATION: PCR Primer SBA1224 which, in conjunction with
      the vector F9HZLC1-1, generates the DNA fragment coding for the
      Campath signal sequence.

<400> SEQUENCE: 39
agactgtgtc agtactatgt cggagtggac acc                                  33

<210> SEQ ID NO 40
<211> LENGTH: 90
<212> TYPE: DNA
<213> ORGANISM: Artificial Sequence
<220> FEATURE:
<223> OTHER INFORMATION: Overlapping synthetic oligonucleotides which,
      when annealed and extended, represent the portion of the light
      chain variable region being altered.

<400> SEQUENCE: 40
gacatagtac tgactcagtc tccaagcagc ctgtctgcgt ctgtaggaga tagagtcacc     60
attacctgca gggccagcca aagtattagc                                      90

<210> SEQ ID NO 41
<211> LENGTH: 101
<212> TYPE: DNA
<213> ORGANISM: Artificial Sequence
<220> FEATURE:
<223> OTHER INFORMATION: Overlapping synthetic oligonucleotides which,
      when annealed and extended, represent the portion of the light
      chain variable region being altered.

<400> SEQUENCE: 41
cccgagatgg actgggaagc atacttgatg agaagcctag gagccttgcc aggtttttgt     60
tgataccagt gtaggtggtt gctaatactt tggctggccc t                        101

<210> SEQ ID NO 42
<211> LENGTH: 99
<212> TYPE: DNA
<213> ORGANISM: Artificial Sequence
<220> FEATURE:
<223> OTHER INFORMATION: Overlapping synthetic oligonucleotides which,
    when annealed and extended, represent the portion of the light
    chain variable region being altered.

<400> SEQUENCE: 42
gcttcccagt ccatctctgg gatcccctcc aggttcagtg gcagtggatc agggacagat      60
ttcactttca ccatcagcag tctacagcct gaagatatt                             99

<210> SEQ ID NO 43
<211> LENGTH: 99
<212> TYPE: DNA
<213> ORGANISM: Artificial Sequence
<220> FEATURE:
<223> OTHER INFORMATION: Overlapping synthetic oligonucleotides which,
    when annealed and extended, represent the portion of the light
    chain variable region being altered.

<400> SEQUENCE: 43
gcttcccagt ccatctctgg gatcccctcc aggttcagtg gcagtggatc agggacagat      60
ttcactttca ccatcagcag tctacagcct gaagatatt                             99

<210> SEQ ID NO 44
<211> LENGTH: 99
<212> TYPE: DNA
<213> ORGANISM: Artificial Sequence
<220> FEATURE:
<223> OTHER INFORMATION: PCR Primer SBA 3170 used to amplify the
    synthetic gene described in SEQ IDS: 40, 41, 42, and 43.

<400> SEQUENCE: 44
gcttcccagt ccatctctgg gatcccctcc aggttcagtg gcagtggatc agggacagat      60
ttcactttca ccatcagcag tctacagcct gaagatatt                             99

<210> SEQ ID NO 45
<211> LENGTH: 33
<212> TYPE: DNA
<213> ORGANISM: Artificial Sequence
<220> FEATURE:
<223> OTHER INFORMATION: PCR Primer SBA 3171 used to amplify the
    synthetic gene described in SEQ IDS: 40, 41, 42, and 43.

<400> SEQUENCE: 45
ttccaccttg gtaccctggc cgaacgtgaa agg                                   33